(12) United States Patent
Kyomoto et al.

(10) Patent No.: US 8,765,265 B2
(45) Date of Patent: *Jul. 1, 2014

(54) POLYMER SLIDING MATERIAL, ARTIFICIAL JOINT MEMBER, MEDICAL APPLIANCE, AND MANUFACTURING METHOD THEREFOR

(75) Inventors: Masayuki Kyomoto, Osaka (JP); Kazuhiko Ishihara, Tokyo (JP)

(73) Assignees: Kyocera Medical Corporation, Osaka (JP); The University of Tokyo, Tokyo (JP)

( * ) Notice: Subject to any disclaimer, the term of this patent is extended or adjusted under 35 U.S.C. 154(b) by 256 days.

This patent is subject to a terminal disclaimer.

(21) Appl. No.: 13/142,058

(22) PCT Filed: Dec. 25, 2009

(86) PCT No.: PCT/JP2009/071614
§ 371 (c)(1),
(2), (4) Date: Oct. 12, 2011

(87) PCT Pub. No.: WO2010/074238
PCT Pub. Date: Jul. 1, 2010

(65) Prior Publication Data
US 2012/0022665 A1   Jan. 26, 2012

(30) Foreign Application Priority Data

Dec. 25, 2008  (JP) .................................. 2008-330504
Dec. 25, 2008  (JP) .................................. 2008-330513

(51) Int. Cl.
  *B32B 27/00* (2006.01)
  *F16C 33/20* (2006.01)

(52) U.S. Cl.
  USPC ..................... 428/500; 623/23.58; 623/23.59; 508/100

(58) Field of Classification Search
  None
  See application file for complete search history.

(56) References Cited

U.S. PATENT DOCUMENTS

| | | | |
|---|---|---|---|
| 6,228,900 B1 | 5/2001 | Shen et al. | |
| 6,653,423 B1 | 11/2003 | Yamamoto et al. | |
| 2004/0243249 A1 | 12/2004 | Ishihara et al. | |
| 2008/0119762 A1 | 5/2008 | Tateishi et al. | |
| 2009/0306781 A1 | 12/2009 | Kyomoto et al. | |
| 2009/0325027 A1* | 12/2009 | Maekawa et al. | 429/33 |
| 2010/0262237 A1 | 10/2010 | Kyomoto et al. | |
| 2011/0004009 A1 | 1/2011 | Itoh et al. | |

FOREIGN PATENT DOCUMENTS

| EP | 2 204 197 | 7/2010 |
|---|---|---|
| JP | 2984203 | 9/1999 |
| JP | 2003-310649 | 11/2003 |
| JP | 2007-202965 | 8/2007 |
| JP | 2007-260247 | 10/2007 |
| JP | 2008-053041 | 3/2008 |
| JP | 2008-054788 | 3/2008 |
| JP | 2008-125523 | 6/2008 |
| WO | 97/29793 | 8/1997 |
| WO | 01/05855 | 1/2001 |
| WO | 2007/063843 | 6/2007 |
| WO | 2007/091521 | 8/2007 |
| WO | 2009/044816 | 4/2009 |

OTHER PUBLICATIONS

Kyomoto et al., Self-initiated surface grafting with poly(2-methacryloyloxyethyl phosphorylcholine) on poly (ether-ether-ketone), Biomaterials 31 (2010) 1017-1024.*

S. Kihara et al., "In Vivo Evaluation of a MPC Polymer Coated Continuous Flow Left Ventricular Assist System", Artificial Organs, vol. 27, No. 2, pp. 188-192, 2003.

S. M. Kurtz et al., "PEEK Biomaterials in Trauma, Orthopedic, and Spinal Implants", Biomaterials, vol. 28, No. 32, pp. 4845-4869, 2007.

E.P.J. Watters et al., "Wear of Artificial Hip Joint Material", Chemical Engineering Journal, vol. 112, No. 1-3, pp. 137-144, Sep. 2005.

English translation of the International Preliminary Report on Patentability and Written Opinion dated Aug. 9, 2011.

Tatsuro Goda et al., "Photografting of 2-methacryloyloxyethyl phosphorylcholine from polydimethylsiloxane: Tunable protein repellency and lubrication property", Colliods and Surfaces B: Biointerfaces, vol. 63, No. 1, 2008, pp. 64-72.

(Continued)

*Primary Examiner* — Sheeba Ahmed
(74) *Attorney, Agent, or Firm* — Wenderoth, Lind & Ponack, L.L.P.

(57) ABSTRACT

Disclosed is a sliding member with excellent durability and capable of maintaining wear resistance over a long period of time. Further disclosed is an artificial joint member for which the film thickness of the polymer base material is reduced. Further disclosed is an artificial joint which is capable of demonstrating high lubricity, biocompatibility, and resistance to dislocation after introduction into the body. Further disclosed are a medical appliance material and a medical appliance which demonstrate excellent biocompatibility. The sliding material or the medical appliance material is formed by a polymer layer or a biocompatible material layer (B) being provided by coating at least a portion of the surface of a polymer base material (A), the surface of which has a ketone group, and the polymer layer or biocompatible layer (B) is characterized by being formed by surface graft polymerization, wherein the polymer base material (A) is immersed in a reaction system which contains a monomer (C), the polymer base material (A) is exposed to light, and polymerization of the monomer is initiated from the surface of the polymer base material (A). Using the sliding material or medical appliance material, an artificial joint member, an artificial joint, a medical appliance material, and a medical appliance are manufactured.

30 Claims, 9 Drawing Sheets

(56) References Cited

OTHER PUBLICATIONS

Extended European Search Report issued Jul. 18, 2013 in corresponding European Patent Application No. 09835034.1.
Masayuki Kyomoto et al., "Self-Initiated Surface Graft Polymerization of 2-Methacryloyloxyethyl Phosphorylcholine on Poly(ether ether ketone) by Photoirradiation", ACS Applied Materials & Interfaces, vol. 1, No. 3, 2009, pp. 537-542, XP008154069.
Masayuki Kyomoto et al., "Self-initiated surface grafting with poly(2-methacryloyloxyethyl phosphorylcholine) on poly(ether-ether-ketone)", Biomaterials, vol. 31, No. 1, 2010, pp. 1017-1024, XP008154073.

* cited by examiner

FT-IR analysis

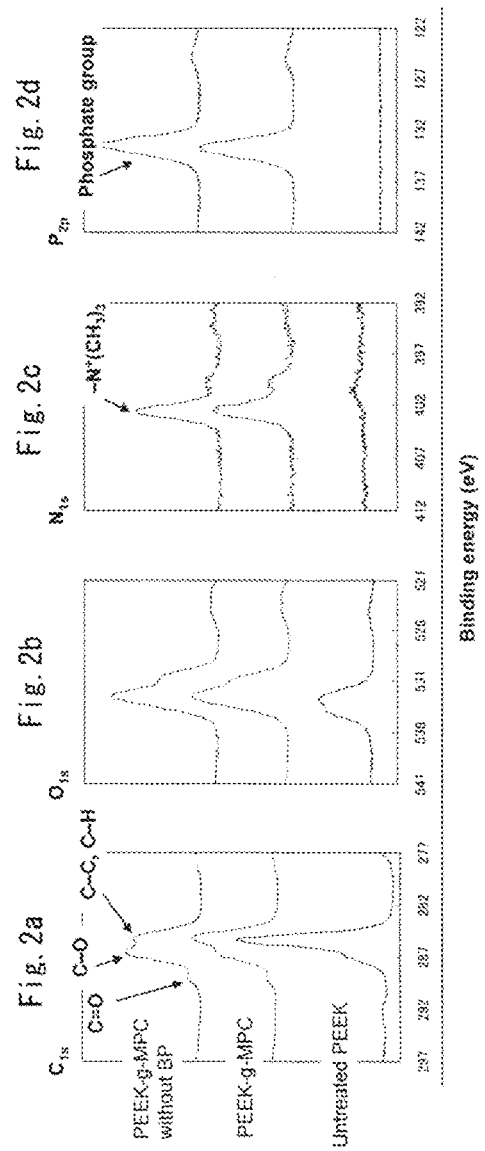

POLYMER SLIDING MATERIAL, ARTIFICIAL JOINT MEMBER, MEDICAL APPLIANCE, AND MANUFACTURING METHOD THEREFOR

TECHNICAL FIELD

The present invention relates to a polymer sliding material to be used as a material for medical materials. The present invention particularly relates to a polymer sliding material which is capable of maintaining the properties of wear resistance, load supportability and fracture resistance for a long period of time, which is applicable to an artificial joint that restores human joints, and artificial joints which are made of the sliding material.

The present invention relates to medical appliances, particularly to medical tools which contact with blood and biotissues inside and/or outside of the body, such as a blood pump for an (auxiliary) artificial heart, an artificial valve, a stent and a pacemaker as well as dental implants.

BACKGROUND ART

In general, polyethylene (mainly ultrahigh molecular weight polyethylene, hereinafter referred to as PE) has been conventionally used as a component member of artificial joints, such as an artificial hip joint and an artificial knee joint. However, when the artificial joint was used in vivo, there was a tendency that lysis of bone (i.e. osteolysis) had been induced by the wear debris of PE which was produced through a frictional movement. When the osteolysis happened, so-called loosening in which the fixing force of an artificial joint and a bone becomes weaker arose, and the loosening had become a big problem as complication of an arthroplasty. Usual abrasion loss of the above-mentioned PE was about 0.1 to 0.2 mm per year, and there was no problem for a certain period of time (for example, for about several years) after the arthroplasty. However, the amount of the above-mentioned loosening became remarkable after a lapse of about five years, and thus a re-operation of exchanging the artificial joint should be needed, and that could impose a heavy burden on the patients.

In the artificial hip joint, the size of a femoral head component has been enlarged for the purpose of improving the range of motion and of prevention of dislocation. Since there is a limit for the size of a cup to be housed in an acetabulum, thinning of (the thickness of) the acetabular cup made of PE has been required corresponding to the enlarging the size of the femoral head component. There was a limit in advancing the thinning of the acetabular cup due to the viewpoints of the properties of wear resistance, deformation resistance and fracture resistance.

One of the solutions for the loosening is to decrease the amount of the wear debris of PE, and to this end extensive researches on crosslinked PE wherein molecular chains are crosslinked thereamong (hereinafter referred to as CLPE) by irradiating PE with an electron beam or a gamma ray have been carried out in recent years (Patent Documents 1 to 3). These researches utilize the matter that irradiating a polymer material with a radiation having high energy such as an electron beam or a gamma ray generates free radicals due to cutoff of molecular chains, followed by occurring the recombination or crosslinking reaction of the molecular chains. The above-mentioned CLPE is excellent in the property of wear resistance compared with the conventional PE, so that it is reported that the amount of the abrasion loss can be reduced even to the order of about one fifth to one tenth of the conventional amount.

On the other hand, intensive researches of alternate material of PE to be used for an artificial joint have also been carried out, thereby polyetheretherketone (hereinafter referred to as PEEK) is taken as an example thereof, which is an engineering plastic excellent in the properties of deformation resistance and fracture resistance. Although the property of wear resistance of PEEK itself is not so sufficient, the property is intended to be improved by compositing PEEK with a carbon fiber. However, use of rigid carbon fiber may damage the femoral head component to be combined therewith, and thus a PEEK material having sufficient properties for the artificial joints has not been obtained.

Alternatively, it has also been studied to improve the property of slidability of the surface of the sliding portion by forming a coating layer on the surface of PE. For example, it is known a method of fixing a coating layer of a random copolymer comprising an allylamine and a group analogous to a phosphorylcholine group to the surface of a medical appliance, which is required to have an excellent sliding property such as an artificial joint, thereby providing a biocompatibility and a surface lubricity thereto (Patent Document 4).

Particularly, an artificial joint component made from a polymeric material which is excellent in reducing the abrasion of the artificial joint and is capable of suppressing the generation of wear debris than ever before can be obtained by grafting a polymerizable monomer having a phosphoryl choline group onto the slidable surface of the artificial joint made from PE (Patent Document 5).

In the conventional photo-graft polymerization method, a photopolymerization initiator, for example, benzophenone (BP) was used. A "grafting from" method, wherein the surface of the substrate is used as the starting point of graft polymerization, is advantageous in achieving high densification of the graft layer compared with the other techniques, and it is necessary to preliminarily apply the polymerization initiator to the surface of the substrate which should be treated in order to realize this method. Patent Document 5 discloses an invention to use CLPE as a substrate, 2-methacryloyloxyethyl phosphorylcholine (MPC) as a monomer and BP as a photopolymerization initiator, thereby causing MPC graft polymerization on the surface of the substrate to form a membrane of a layer or MPC on the surface thereof.

The MPC polymer produced by the method of Patent Document 5 is useful as the material for forming an ideal biocompatible surface. However, in the case where the product therefrom is used as a biocompatible material, it is desirable that no photopolymerization initiator remains on the surface of the substrate and in the graft polymer layer after performing the graft polymerization reaction. Therefore, according to the method of Patent Document 5, there was another problem that the radical initiator remaining after performing the graft polymerization reaction should be removed from the surface of the substrate and the graft polymer layer.

It is reported that there are the methods of generating radicals using high-energy radiations, for example, a gamma ray, an electron beam (beta ray), an ionic beam, an X-ray and so on as the methods of performing the graft polymerization without using the polymerization initiator (Patent Document 6).

On the other hand, metal materials used for the medical appliance (for example, an artificial kidney, an artificial lung, an artificial trachea, and a blood pump for an (auxiliary) artificial heart, an artificial valve, an artificial blood vessel, a catheter, a cardiac pacemaker, an artificial bone, an artificial tendon, an artificial knuckle and a bone securing plate, a bone screw and so on) almost satisfies the condition of the mechanical properties, but they are not always sufficient to the biocompatibility (including the hemocompatibility). For example, when blood components produce thrombus by contacting with the surface of the medical appliance, they could inhibit the blood flow and thereby could seriously harm the human body. Therefore, an agent which suppresses the protective response of the body is required in therapeutic interventions using the medical appliance in clinical practice. Side effects caused by prolonged use of the above-mentioned agent are serious problems. For example, side effects caused by frequent use of anticoagulant agents include internal bleeding in the skin, nose bleeding, bleeding from the gums, excessive bleeding from the wound, bleeding such as hypermenorrhea, bloody sputum, hematuria, hematochezia as well as dizziness and wobble. Particularly, bleedings such as gastrointestinal bleeding, intracranial bleeding and intraperitoneal bleeding may place the patient's life in peril when finding of such bleedings would be delayed. For the developments of the medical appliance which can be embedded in a living body and used therein for a long period of time, a material having the biocompatibility (including the hemocompatibility) is essential.

In the present medical practice, a method to use a biologically active substance capable of inhibiting thrombus formation is used so as to impart antithrombotic properties to a surface of a medical device, for example, an artificial organ. To this end, there is a method of fixing a biologically active substance such as urokinase having a function of dissolving thrombus thus formed, heparin capable of inhibiting a function of thrombin as a coagulation factor, or prostaglandin as a platelet activation inhibitor to a surface of a material. However, the side effects caused by these agents can not be disregarded and is a big problem. In addition, it is extremely difficult to control the releasing rate of the agent and the effects therefrom cannot be expected after release of the agents. Most of the drug eluting type medical appliance (particularly stent) use a non-biodegradable polymers including, for example, poly(n-butyl methacrylate), poly(dimethyl siloxane) and so on. Thus, it is reported that polymers which remain on the surface of the stent after the drug eluted may cause an inflammatory reaction and/or a thrombus formation, and also cause a problem of failing to endothelize on the surface of the stent.

In order to impart antithrombotic properties to the surfaces of the medical appliance, for example, the artificial organ, a method utilizing a biological reaction is employed. That is, it is a method in which coagulation factors and platelets are moderately aggregated to a surface of a material to form a thrombus membrane, and endothelial cells constituting a vascular wall are engrafted on the thrombogenic membrane as a footing and a thin neointima is formed on the surface of the material by further growth of the endothelial cells. However, there is a possibility that a thrombus may occur during the period of about one month after an operation until endothelial cells will cover a medical appliance. Then, it became necessary to administer an antiplatelet drug and thus the side effect caused by the drug cannot be neglected.

Furthermore, there is also employed a method in which antithrombotic properties are obtained by surface properties of the material per se without using a biologically active substance or a drug. By the way, thrombus formation occurs due to an adsorption of a plasma protein and a subsequent activation of platelets, and the adsorption of the plasma protein onto the surface of the material physicochemically proceeds. Then, in order to prevent formation of thrombus, it is important to make the interaction between the material and blood as little as possible. Thus, it is desirable to convert the surface of the material into the state almost as close to blood as possible by reforming the surface thereof in order to decrease the above interaction.

Such a reforming method includes, for example, a method in which a water-soluble polymer is bonded by a coupling reaction utilizing functional groups such as hydroxyl and amino groups of the surface of the material.

For example, a method of fixing a random copolymer which consists of an allylamine and a group analogous to a phosphorylcholine group for a medical material is disclosed (Patent Document 7). When the copolymer is used as in the above method, the content of the phosphorylcholine group on the surface of the medical material decreases, thereby causing a problem that each of the biocompatibility (including the hemocompatibility), the hydrophilicity and the surface lubricity could not be attained to a satisfactory extent. On the other hand, when the content of the phosphorylcholine group in the copolymer is excessive, there arises another problem that the copolymer becomes soluble in water and adhesion thereof would not be maintained when used for a long period of time. Actually, it is reported that, in an artificial heart which was coated with an MPC copolymer, merely 5% of MPC copolymer remained after use thereof for ninety-one days (Non-Patent Document 1).

Another reforming method includes a method in which peroxide as a polymerization initiator is produced on a surface of a material by irradiating with ultraviolet rays, electric beams or ion beams in the presence of oxygen, and then a water-soluble vinyl monomer is subjected to radical polymerization to form a water-soluble polymer chain on the surface of the material. It is reported that this water-soluble polymer chain prevents a protein from being directly contacted with the surface of the material and inhibits the adsorption of the protein onto the surface of the material.

For example, it is reported that anti-protein adsorption property can be improved by grafting MPC as a monomer on a polyethylene surface through irradiation with ultraviolet rays (Patent Document 8). According to the method of Patent Document 2, it is designed to improve the wear resistant property of a substrate through imparting the surface of the substrate with highly slidability by causing graft polymerization of MPC onto PE using PE without ketone group as the substrate, MPC as a reactive monomer and BP as a photopolymerization initiator.

Taking a dental implant into account, there has conventionally been carried out a prosthetic treatment with retrievable partial denture or bridge denture for repairing a loss of teeth due to periodontal diseases and dental caries. However, retrievable partial denture has an aesthetic problem attributed from a metal hook and a problem of providing a feeling of resistance to implementation, while bridge denture has a problem that burden for abutment tooth to be ground cannot be avoided. A dental implant treatment has attracted special interest recently as a prosthetic treatment and is one of selection choices, and the number of cases has remarkably increased. In loss of teeth due to fracture of an alveolar bone, teeth are lost together with the alveolar bone around teeth and thus bone width and bone height enough to carry out embedding of implant were not often obtained. However, it has become possible to apply a bone grafting method, a guided bone regeneration (GBR) method, a bone lengthening method, a bone prosthetic material, and a bone augmentation method utilizing cytokines, thus increasing the number of cases of application of a dental implant. In some cases, it becomes possible to impart an occlusion function through embedding due to one-stage implant and mounting of an upper structure at an initial stage after embedding, by improving surface properties of an implant or controlling a load on an implant body after embedding. Establishment of a method of early and surely acquiring oseointegration remarkably contributes to stabilization of the occlusion function of the dental implant. However, even if oseointegration is acquired, it is impossible to persistently avoid the circumstance in which the implant body as foreign matters penetrates through the epithelium. Therefore, how plaque deposition in this gingival penetration portion is inhibited and inflammation around the implant body is prevented, was an important object for enabling the dental implant to function over a long period. Particularly in two-stage implant, the micro-gap existing between the abutment and the fixture bonding portion makes it easy to cause inflammation around the implant. Also, local bone resorption temporarily occurs due to a removal of the bond formed on so-called healing cap or the top portion of the implant body during secondary surgery, and thus down growth of gingival epithelia is likely to occur, thus leading to the situation where plaque deposition is likely to occur, and which situation becomes similar to periodontal diseases, thereby being obliged to remove the dental implant in some situations, which could arise a clinical problem.

Patent Document 1: Japanese Patent No. 2984203
Patent Document 2: U.S. Pat. No. 6,228,900
Patent Document 3: International Publication No. WO97/29793
Patent Document 4: International Publication No. WO01/05855
Patent Document 5: Japanese Unexamined Patent Publication (Kokai) No. 2003-310649
Patent Document 6: Japanese Unexamined Patent Publication (Kokai) No. 2008-53041
Patent Document 7: International Publication No. WO01/05855
Patent Document 8: Japanese Unexamined Patent Publication (Kokai) No. 2007-202965
Nonpatent Document 1: In Vivo Evaluation of a MPC Polymer Coated Continuous Flow Left Ventricular Assist System, ARTIFICIAL ORGANS, VOL 27, No. 2, 2003

DISCLOSURE OF THE INVENTION

Problems to be Solved by the Invention

The above-mentioned CLPE shows an excellent wear resistant property rather than PE, but the period of use thereof is so short that it is not sufficiently confirmed whether it can maintain the wear resistant property for a long period of time. When CLPE or surface-modified PE is used for the material of an artificial joint, it may be expected to show an excellent wear resistant property. However, there is no improvement in the mechanical property of the substrate since the substrate itself is still made of PE or CLPE. Thus, there remained a problem that thinning of the acetabular cup has a limitation according to the viewpoints of the properties of deformation resistance and fracture resistance.

Moreover, when the technique of fixing the coating layer of the random copolymer to the surface of the medical appliance made of PE according to Patent Document 4 would be applied to a sliding member of an artificial joint, it is highly possible that the coating layer of the random copolymer would be peeled from the surface of PE under the rigorous friction and wear environment, so that it is difficult to put it into practical use. It is conceivable that these peeling could be resulted from the low bonding force between the surface of PE and the coating layer of the random copolymer. According to the above method, the coating layer of the random copolymer wherein the polymerization reaction has been sufficiently advanced is designed to immobilize to the surface of PE. However, there is no functional group for bonding with the coating layer of the random copolymer to be polymerized on the surface of the PE, and thus a sufficient bonding force seems not to be obtained.

On the other hand, the invention of Patent Document 5 succeeded in improving the bonding force between a polymer chain having a phosphoryl choline group and the surface of PE by graft bonding the polymer chains onto the surface of PE.

The method of Patent Document 5 is shown by the following scheme 1:

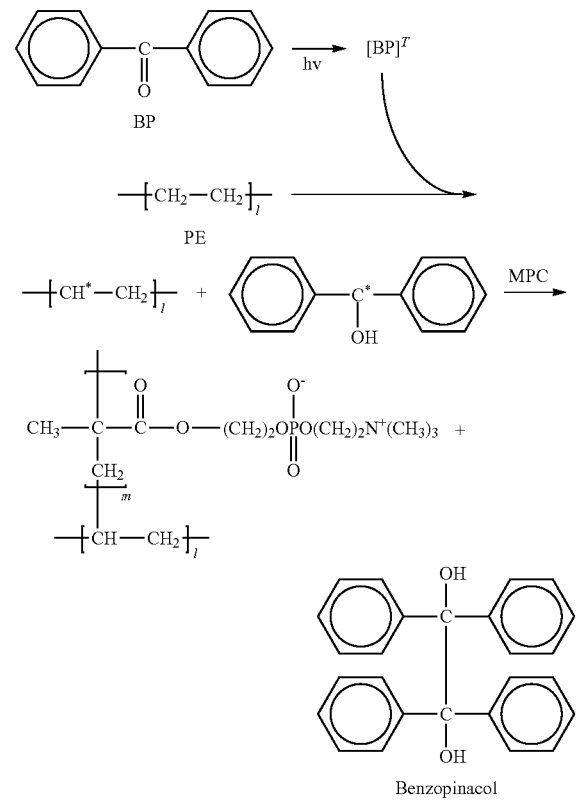

According to the method of Patent Document 5, a sliding member of a joint wherein a wear-resistant coating, which hardly peels off even under the rigorous friction and wear environment, is formed on the sliding surface of PE can be obtained, but the substrate is still made of PE. Therefore, there remained a problem that thinning of the acetabular cup has a limitation according to the viewpoints of the properties of deformation resistance and fracture resistance as with the case of the untreated PE and the other surface-modified PE.

The method of Patent Document 6 which do not use the polymerization initiator uses a high-energy radiation, and such a high-energy radiation per se has an increased risk. Furthermore, a large-scale and a special equipment is required for management of the radiation source, so that there is a problem in respect of the safety and the economical efficiency.

According to the simultaneous irradiation method proposed by Patent Document 6 as a specific method for graft polymerization, a sufficient grafting density could not be obtained in the graft polymerization due to generating radicals from both of the substrate and the monomer and unnecessary or undesired breakage of molecular chains could occur inside the substrate since the radiation such as gamma ray could penetrate to inside the substrate. Thus, there is a problem that the substrate could be degraded or embrittled by the method.

According to the pre-irradiation method proposed by Patent Document 6 as another method for graft polymerization, as the period of time after irradiation until the substrate, in which radicals generated, contacts with the monomers, the amount of the available radicals decreases. Thus, there is a possibility of failing to obtain a desired and sufficient grafting density (for example, 0.01 chains/nm$^2$ or more). There also remains a problem that the substrate degrades (or embrittles) along with the irradiation of the radiation such as gamma ray. The grafting density is described in "New Frontiers in Polymer Synthesis" Advances in Polymer Science, VOL. 217, 2008.

Therefore, it is an object of the present invention to dissolve the above problems accompanied by providing the sliding member having an excellent durability, which is capable of maintaining the wear resistant property for a long period of time. It is another object of the present invention to improve the safety and economical efficiency during the production process of the sliding members, the artificial joint component or the artificial joint. It is another object of the present invention to provide the artificial joint which is designed to advance thinning of the polymer substrate. It is a further object of the present invention to provide an artificial join, which can demonstrate a high lubricity, a biocompatibility and an anti-dislocation function after introduced into the human body.

According to the methods proposed by Patent Document 7 and non-patent document 1, the ratio (or the density) of the phosphoryl choline group, which coat the surface of the substrate, fell below the desired extent in each case. It is also an object of the present invention to provide a medical appliance material that shows desired and excellent biocompatibility (including hemocompatibility), hydrophilicity and surface lubricity in the surface of the medical appliance when a monomer having phosphoryl choline group, particularly MPC is used.

The method of Patent Document 8 is shown by the scheme 1 illustrated above.

According to the method of Patent Document 8, the substrate is still made of PE, so that there is a certain limitation in reduction in thickness and in weight of the substrate in order to secure a sufficient strength of the substrate. Thus, it is yet another object of the present invention to design the reduction in thickness and/of in weight of the substrate, while to provide a medical appliance material which is capable of exerting a desired strength.

The present invention has been made in consideration of the above-mentioned problems and has the object of providing a medical appliance excellent in antithrombotic property and slidability, which hardly forms thrombus and the like, thereby for example, being capable of eliminating use of the drugs inhibiting a biological defense reaction, even where the appliance directly contacts with the biotissues inside and/or outside of the body and such a condition is maintained for a long period of time, and the production method therefor. It is desirable that the above medical appliance is excellent for the functions such as cellular adhesion inhibiting potency, biocompatibility, antibacterial properties (inhibition of biofilm formation and adhesion) and so on. Furthermore, it is yet another object of the present invention to provide a dental implant, which demonstrates cellular adhesion inhibiting effect and which is capable of inhibiting the periodontal diseases and the deposition of dental plaque.

Means for Solving the Problems

The inventors, on the one hand, focused on the matter that a membrane obtained through polymerizing the monomers containing phosphoryl choline groups shows similar behavior to the cellular membrane, and on the other hand, found the matter that the monomers having vinyl groups such as acrylates can be graft polymerized on the surface of the polymer substrate having ketone groups thereon, and then the above objects have been attained by combining the above matters.

The present application provides, as a first invention, an invention of a polymer sliding material comprising a polymer substrate (A) having ketone groups on the surface thereof and a coating layer (B) which coats at least a portion of the surface of the polymer substrate (A), wherein the coating layer (B) is formed by a surface graft polymerization comprising immersing the polymer substrate (A) in a reaction system containing a monomer (C), irradiating the polymer substrate (A) with light, thereby polymerizing the monomer from the surface of the substrate.

The present application provides, as a second invention, an invention of an artificial joint component made of the polymer sliding material of the first invention, wherein a polymer substrate (A) constructs the proximal of the artificial joint component, and a coating layer (B) is formed on at least the sliding face of the artificial joint component.

The present application provides, as a third invention, an invention of an artificial joint, which is made of the artificial joint component of the above second invention.

The present application provides, as a fourth invention, an invention of a medical appliance material comprising a biocompatible material layer (B) covering at least a portion of the surface of the polymer substrate (A) having ketone groups on the surface thereof, wherein the biocompatible material layer (B) is formed by a surface graft polymerization comprising immersing the polymer substrate (A) in a reaction system containing a monomer (C), irradiating the polymer substrate (A) with light, thereby polymerizing the monomer from the surface of the substrate.

The present application provides, as a fifth invention, an invention of a medical appliance produced with using the medical appliance material of the above fourth invention.

The present application provides, as a sixth invention, an invention of a method of producing a medical appliance material comprising a polymer substrate (A) and a coating layer (B) which coats at least a portion of the surface of the polymer substrate (A), the method comprising immersing a polymer substrate (A) in a reaction system containing a monomer (C) for forming a biocompatible material layer (B), irradiating the polymer substrate (A) with light, thereby initiating the polymerization of the monomer from the surface of the polymer substrate (A), wherein the polymer substrate (A) is a polymer having ketone groups on the surface thereof, and the reaction system containing the monomer (C) as well as the surface and the inside of the polymer substrate (A) includes no polymerization initiator.

These inventions of the present application have been accomplished based on the confirmation performed by the present inventors that when a monomer having vinyl group is graft polymerized through the surface-starting graft polymerization, i.e. the "grafting from" method, a covalent bonding having a favorable and high bonding may be formed between a polymer layer (or a polymer film) or a biocompatible material layer obtained from the graft polymerization and a polymer substrate, and a desired polymerization reaction may be performed without using a polymerization initiator by using a particular kind of polymer as the polymer substrate.

The polymer sliding material of the first invention, in one embodiment, may be characterized in that the coating layer (B) is formed through the graft polymerization without including a polymerization initiator in the surface and inside of the polymer substrate (A) and the reaction system containing the monomer (C). The polymer sliding material of the first invention, in one embodiment, can be characterized in that the polymer substrate (A) is the polymer substrate having an aromatic ketone.

In the polymer sliding material of the first invention, in one embodiment thereof, the polymer substrate (A) is a polymer selected from the group consisting of polyether ketone (PEK), PEEK, polyether ketone ketone (PEKK), Polyetheretherketone ketone (PEEKK), polyether ketone ether ketone ketone (PEKEKK) and poly aryl ether ketone (PAEK), a composited polymer wherein at least two kinds of polymers from the above group are composited, and a fiber-reinforced polymer formed by a polymer selected from the above polymer and the composited polymer. In the polymer sliding material of the first invention, in one embodiment thereof, the monomer (C) is selected from (meth)acrylate compounds.

In the polymer sliding material of the first invention, in one embodiment thereof, the monomer (C) is at least a compound selected from the group consisting of an epoxy(meth)acrylate compound, an urethane (meth)acrylate compound, a polyester (meth)acrylate compound, a polybutadiene (meth)acrylate compound and a silicone (meth)acrylate compound. In the polymer sliding material of the first invention, in one embodiment thereof, the monomer (C) contains a compound having a phosphoryl choline group.

In the polymer sliding material of the first invention, in one embodiment thereof, the compound having a phosphoryl choline group is MPC. In the polymer sliding material of the first invention, in one embodiment thereof, the surface graft polymerization was performed in a solvent which disperses or dissolves the monomer (C) without dissolving the polymer substrate (A).

The polymer sliding material of the first invention, in one embodiment thereof, shows the coefficient of dynamic friction in a range from 0.01 to 0.04 under the load of 0.98N, the slide distance of 25 mm, the bounce frequency of 1 Hz, the room temperature and the water lubrication environmental condition.

In the polymer sliding material of the first invention, in one embodiment thereof, the polymer substrate (A) constructs at least a portion of an artificial joint component, for example, the whole or a part of the acetabular cup and/or the whole or a part of the bone head portion of the artificial joint. In the polymer sliding material of the first invention, in one embodiment thereof, the coating layer (B) has a thickness of 10 to 200 nm. In the polymer sliding material of the first invention, in one embodiment thereof, the surface of the sliding material shows a static water-contact angle of not more than 20° using a sessile drop method under the conditions in which the contact angle was measured after 60 seconds. In the polymer sliding material of the first invention, in one embodiment thereof, each concentration of a phosphorus atom and a nitrogen atom on the surface of the sliding material measured by X-ray photoelectron spectroscopy is not less than 4 atom %. An artificial joint component of the second invention, in one embodiment thereof, is an artificial joint component produced by polymer sliding material of the first invention, wherein the polymer substrate (A) constructs the base portion of the artificial joint component and at least a sliding face of the artificial joint component is coated with a coating layer (B). In the polymer sliding material of the second invention, in one embodiment thereof, the ball head to be combined has a thickness of not less than 32 mm and the polymer substrate has a thickness in the range from 3 to 6 mm. An artificial joint of the third invention, in one embodiment thereof, can be characterized by being formed from the artificial joint component.

In the medical appliance material of the fourth invention, in one embodiment thereof, a biocompatible material layer (B) is formed through the graft polymerization without including a polymerization initiator in the surface and inside of the polymer substrate (A) and the reaction system containing the monomer (C).

In the medical appliance material of the fourth invention, in one embodiment thereof, the polymer substrate (A) is the polymer substrate that contains an aromatic ketone.

In the medical appliance material of the fourth invention, in one embodiment thereof, the polymer substrate (A) is a polymer selected from the group consisting of PEK, PEEK, PEKK, PEEKK, PEKEKK and PAEK, a composited polymer wherein at least two kinds of polymers from the above group are composited, and a fiber-reinforced polymer formed by a polymer selected from the above polymer and the composited polymer.

In the medical appliance material of the fourth invention, in one embodiment thereof, the monomer (C) is selected from (meth)acrylate compounds.

In the medical appliance material of the fourth invention, in one embodiment thereof, the monomer (C) is at least one compound selected from the group consisting of an epoxy (meth)acrylate compound, an urethane (meth)acrylate compound, a polyester (meth)acrylate compound, a polybutadiene (meth)acrylate compound and a silicone (meth)acrylate compound.

In the medical appliance material of the fourth invention, in one embodiment thereof, the monomer (C) contains a compound having a phosphoryl choline group.

In the medical appliance material of the fourth invention, in one embodiment thereof, the compound having a phosphoryl choline group is MPC.

In the medical appliance material of the fourth invention, in one embodiment thereof, the surface graft polymerization was performed in a solvent which disperses or dissolves the monomer (C) without dissolving the polymer substrate (A).

In the medical appliance material of the fourth invention, in one embodiment thereof, the surface of the biocompatible material layer (B) shows the coefficient of dynamic friction in a range from 0.01 to 0.04, preferably from 0.01 to 0.02 using a Pin-on-plate type friction tester under the load of 0.98N, the slide distance of 25 mm, the bounce frequency of 1 Hz, the room temperature and the water lubrication environmental condition.

In the medical appliance material of the fourth invention, in one embodiment thereof, the biocompatible material layer (B) has a thickness of 10 nm to 1 micrometer, preferably at least 50 nm, more preferably at least 100 nm up to about 250 nm, more preferably up to about 200 nm.

In the medical appliance material of the fourth invention, in one embodiment thereof, the surface of the biocompatible material layer (B) shows a static water-contact angle of not more than 40°, preferably not more than 20°, more preferably not more than 10° using a sessile drop method under the conditions in which the contact angle was measured after 60 seconds.

In the medical appliance material of the fourth invention, in one embodiment thereof, the surface each concentration of a phosphorus atom and a nitrogen atom on the surface of the biocompatible material layer (B) measured by X-ray photoelectron spectroscopy is not less than 4 atom %, preferably not less than 4.5 atom %, more preferably not less than 5.0 atom %.

In the medical appliance material of the fourth invention, in one embodiment thereof, the adsorption of protein (albumin or fibrinogen) of the surface of the biocompatible material layer (B) obtained through the micro BCA method is not more than 0.2 microgram/cm$^2$, preferably not more than 0.1 microgram/cm$^2$, more preferably not more than 0.08 microgram/cm$^2$.

In relation to the fifth invention, a medical appliance can be formed by forming a portion, which forms the fundamental skeleton of each medical appliance, is made of a polymer substrate (A), and coating a portion of the surface of the polymer substrate (A), which may directly contact with the biotissues including blood and body fluid, with a biocompatible material layer (B).

Therefore, the medical appliance of the fifth invention, in one embodiment thereof, is selected from the group consisting of an artificial kidney, an artificial lung, an artificial trachea, and a blood pump for an (auxiliary) artificial heart, an artificial valve, an artificial blood vessel, a catheter, a cardiac pacemaker, a dental implant, an artificial tooth, an artificial bone, an artificial tendon, an artificial knuckle, a bone securing plate, a bone screw and so on.

In relation to the production method of the medical appliance of the sixth invention, a biocompatible material layer (B) is formed through the graft polymerization without including a polymerization initiator in the surface and inside of the polymer substrate (A) and the reaction system containing the monomer (C).

In relation to the production method of the medical appliance of the sixth invention, the polymer substrate that contains an aromatic ketone is used as the polymer substrate (A).

In relation to the production method of the medical appliance of the sixth invention, any polymer selected from the group consisting of PEK, PEEK, PEKK, PEEKK, PEKEKK and PAEK, a composited polymer wherein at least two kinds of polymers from the above group are composited, and a fiber-reinforced polymer formed by a polymer selected from the above polymer and the composited polymer is used as the polymer substrate (A). In relation to the production method of the medical appliance of the sixth invention, the monomer (C) is selected from (meth)acrylate compounds.

In relation to the production method of the medical appliance of the sixth invention, the monomer (C) is at least one compound selected from the group consisting of an epoxy (meth)acrylate compound, an urethane (meth)acrylate compound, a polyester (meth)acrylate compound, a polybutadiene (meth)acrylate compound and a silicone (meth)acrylate compound.

In relation to the production method of the medical appliance of the sixth invention, the monomer (C) contains a compound having a phosphoryl choline group. In relation to the production method of the medical appliance of the sixth invention, the compound having a phosphoryl choline group is MPC.

In relation to the production method of the medical appliance of the sixth invention, the surface graft polymerization was performed in a solvent which disperses or dissolves the monomer (C) without dissolving the polymer substrate (A).

Effects of the Invention

According to the first invention of the present application, the polymer substrate and the coating layer formed through polymerizing monomers are bonded (covalently bonded) by graft polymerization, so that a polymer sliding material which can be manufactured safely and economically and is excellent in the durability, which is capable of maintaining the wear resistant property for a long period of time, can be provided. In particular, according to the first invention, a polymer sliding material excellent in the durability, which is capable of preventing remarkable decrease of the wear resistant property for a long period of time such as over five to ten years when applied to an artificial joint can be provided. Since a polymer substrate having ketone groups on the surface thereof, such as PEEK, which is an engineering plastic which is excellent in deformation resistance and fracture resistance, is used as the polymer substrate, a polymer sliding member having less thickness can be provided, while attaining a sufficient wear resistance property, load support property and fracture resistance property even when the thickness of the polymer substrate would be made relatively thinner.

According to the second invention of the present application, the artificial joint component having the properties of the polymer sliding material of the above first invention can be provided.

According to the second invention of the present application, the polymer substrate and the coating layer formed through polymerizing monomers are bonded (covalently bonded) by graft polymerization, so that an artificial joint component which can be manufactured safely and economically and is excellent in the durability, which is capable of maintaining the wear resistant property for a long period of time, can be provided. In particular, according to the second invention, an artificial joint component excellent in the durability, which is capable of preventing remarkable decrease of the wear resistant property for a long period of time such as over five years when applied to an artificial joint can be provided. Since a polymer substrate having ketone groups on the surface thereof, such as PEEK, which is an engineering plastic which is excellent in deformation resistance and fracture resistance, is used as the polymer substrate, an artificial joint member having less outer diameter can be provided, while attaining a sufficient load support property and fracture resistance property even when the thickness of the polymer substrate would be made relatively thinner.

According to the third invention of the present application, the artificial joint having the properties of the artificial joint member of the above second invention can be provided.

The polymer sliding material of the first invention can demonstrate the durability and slidability (good wettability to water, a low coefficient of dynamic friction and a low coefficient of static friction) by coating the given surface of the polymer substrate that can show desired function and characteristics (for example, durability, load support property and deformation resistance) with a layer of a polymer product having desired function and characteristics (for example, high hydrophilicity, lubricity, protein adsorption inhibition property, cellular adhesion inhibiting effect, water resistance, heat resistance).

According to the invention of the medical appliance material of the present application, a strong bond between the polymer substrate (A) and the biocompatible material layer (B) can be maintained over a long period of time, since the polymer substrate and the biocompatible material layer, which were formed by polymerizing the monomers, are covalently bonded by the graft polymerization. The biocompatible material layer (B) formed on the polymer substrate (A) demonstrates an excellent biocompatibility by showing the property which is similar to that of a cell membrane, while can show an excellent anti-thrombus property. Therefore, the medical appliance material obtained can maintain the outstanding biocompatibility, anti-thrombus property, cell adhesion inhibition property, biofilm formation inhibition property, and antibacterial property over a long period of time. The medical appliance formed using the medical appliance material can also maintain the same outstanding characteristics such as biocompatibility, anti-thrombus property, cell adhesion inhibition property, biofilm formation inhibition property and antibacterial properties over a long period of time.

The above medical appliance materials can eliminate the efforts and the necessity to separate and remove the residual components of the polymerization initiator from the polymerized product, when the graft polymerization is performed in the absence of the polymerization initiator on the surface and inside the polymer substrate (A) and the reaction system during polymerization. Furthermore, when a slight amount of the polymerization initiator remains in the biocompatible material layer and the biocompatible material layer contacts with biotissues, there is a possibility that the medical appliance (having the biocompatible material layer) may damage the health of the patient, to whom the medical appliance is applied. However, such a possibility that may damage the health of the patient can be substantially prevented or excluded by the medical appliance of the present invention.

The medical appliance material uses the polymer substrate having ketone groups on the surface thereof, such as PEEK, which is an engineering plastic which is excellent in deformation resistance and fracture resistance, as the polymer substrate, so that a polymer substrate having less thickness may be formed, while attaining a sufficient wear resistance, load support property and fracture resistance property, even when the thickness of the polymer substrate would be made relatively thinner. Therefore, the medical appliance formed using the medical appliance material can attain further downsizing and/or further thinning and/or further light-weighting.

According to the sixth invention of the present application, the medical appliance material and the medical appliance each of which shows excellent anti-thrombus property, cell adhesion inhibition property, biocompatibility and biofilm formation inhibition property, antibacterial properties as well as safety and durability as mentioned above can be produced comparatively economically.

The medical appliance material in the fourth invention can demonstrate the durability and slidability (good wettability to water, a low coefficient of dynamic friction and a low coefficient of static friction) by coating the given surface of the polymer substrate that can show desired function and characteristics (for example, durability, load support property and deformation resistance) with a layer of a polymer product having desired function and characteristics (for example, high hydrophilicity, lubricity, protein adsorption inhibition property, cellular adhesion inhibiting effect, water resistance, heat resistance).

When the medical appliance is made of using the medical appliance material in the fourth invention or according to the method of sixth invention, the medical appliance excellent in antithrombotic property and slidability, which hardly forms thrombus and the like, thereby for example, being capable of eliminating use of the drugs inhibiting a biological defense reaction, even where the appliance directly contacts with the biotissues inside the body. In particular, in the dentistry field, it is capable of providing a medical appliance as a dental implant, which demonstrates cellular adhesion inhibiting effect and which is capable of inhibiting the periodontal diseases and the deposition of dental plaque.

BRIEF DESCRIPTION OF THE DRAWINGS

FIG. 2 shows the results of the XPS analysis (spectrum) of the products of Example 1 and Example 3.

BEST MODE FOR CARRYING OUT THE INVENTION

Figure 1B:
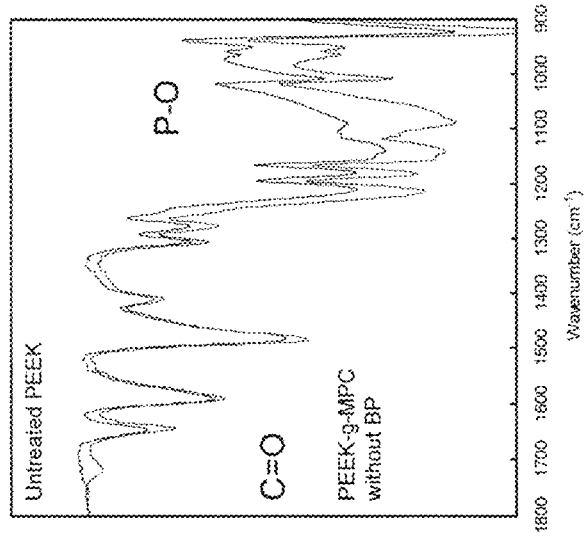
FIG. 1 shows the results of the Fourier transform infrared spectrophotometry (FT-IR) of the products of Example 1 and Comparative Example 3, each of which is compared with an untreated PEEK substrate.

The graft polymerization method used in the present invention is basically characterized in that the surface of the polymer substrate (A) having a ketone group on the surface thereof is used as a reaction field, wherein a reaction system including the monomer (C) is made to exist on the surface of the polymer substrate (A). The present graft polymerization method is also characterized in that it uses no polymerization initiator, for example, no photo radical type initiator. When the polymer substrate is irradiated with light, and thereby performing the surface-initiated graft polymerization in which the polymerization of the monomer is initiated from the surface of the polymer substrate (A), the desired polymerization product can be obtained. The solvent may be used or not depending on the combination of the polymer substrate (A) and the monomer (C). However, in order to cause a radical reaction to occur uniformly in the reaction system as a whole, it is preferable to disperse or dissolve the radical monomer (C) in a suitable solvent. The reaction system in such a case includes the solvent in which the monomer (C) is dispersed or dissolved. It is preferable to use a suitable solvent for the above-mentioned graft polymerization reaction system. A polymerization product (branched polymer) is formed on the substrate (trunk) by the graft polymerization, wherein a covalent bond exists between the substrate and the polymerization product.

In the present graft polymerization method, a substrate having an aromatic ketone can be used as the polymer substrate (A) which has a ketone group on the surface thereof. As an example of such a substrate containing the aromatic ketone, a polymer material selected from the group consisting of PEK, PEEK, PEKK, PEEKK, PEKEKK and PEAK can be mentioned. In order to improve desired functions, characteristics (for example, durability, load support characteristics and deformation resistance), the substrate may be composited with a carbon fiber such as polyacrylonitrile. The ratio of the carbon fiber is preferably in the range from 30 to 60%, and further preferably in an amount of 30%.

In the present graft polymerization method, a vinyl compound, for example, (meth)acrylate compound can be used as the monomer (C). Although the monomer generally has a radical reactivity, it may have the other reactivity, for example, an ionic reactivity (cationic reactivity or anionic reactivity).

In the present graft polymerization method, the (meth) acrylate compound can be copolymerized by using independently or in combination with a plurality of compounds. It is capable of producing the polymerization product as the copolymer of a (meth)acrylate compound and a malediction compound by using a mixture with a vinyl compound and a malediction compound depending on the necessity.

The above monomer includes, for example, (meth)acrylic acid; an alkyl(meth)acrylic acid such as methyl(meth)acrylate, ethyl(meth)acrylate, n-propyl(meth)acrylate, isopropyl (meth)acrylate, n-butyl(meth)acrylate, isobutyl (meth)acrylic acid, tert-butyl(meth)acrylate, n-pentyl (meth)acrylate, n-hexyl(meth)acrylate, cyclohexyl (meth)acrylate, n-heptyl(meth)acrylate, n-octyl (meth)acrylate, 2-ethylhexyl (meth)acrylate, nonyl (meth)acrylate, decyl(meth)acrylate, dodecyl(meth)acrylate, stearyl(meth)acrylate; phenyl(meth)acrylate, tolyl (meth)acrylate, benzyl(meth)acrylate; (meth) acrylic acid alkoxy ester such as 2-methoxy ethyl(meth)acrylate, 3-methoxy butyl(meth)acrylate, 2-hydroxyethyl(meth) acrylate, 2-hydroxypropyl(meth)acrylate; glycidyl(meth) acrylate; 2-aminoethyl(meth)acrylate, (meth)acrylates containing a silane compound such as gamma-methacryloxypropyltrimethoxysilane; ethyleneoxide adducts of (meth) acrylic acid; fluorine-containing (meth)acrylate such as trifluoromethylmethyl(meth)acrylate, 2-trifluoromethylethyl (meth)acrylate, 2-perfluoroethylethyl(meth)acrylate, 2-perfluoroethyl-2-perfluorobutylethyl(meth)acrylate, 2-perfluoroethyl(meth)acrylate, perfluoromethyl (meth)acrylate, diperfluoromethylmethyl(meth)acrylate, 2-perfluoromethyl-2-perfluoroethylmethyl(meth)acrylate, 2-perfluorohexylethyl(meth)acrylate, 2-perfluorodecylethyl (meth)acrylate, 2-perfluorohexadecylethyl(meth)acrylate. Particularly, it is preferable that the monomer includes a compound having a phosphoryl choline group. The compounds having a phosphoryl choline group includes 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, omega-methacryloyloxyethylene phosphorylcholine, 4-styryloxybutyl phosphorylcholine and the like.

Particularly, the compounds having a phosphoryl choline group includes MPC. Especially MPC is preferable. The used amount of the reaction system containing the monomer is from 0.01 to 10 ml, preferably, for example, from 0.01 to 5 ml per square cm of surface area of the polymer substrate. It is preferable that the monomer concentration is from 0.25 to 1.00 mol/L, and more preferably from 0.25 to 0.50 mol/L.

In the case where the compound having the phosphorylcholine group is MPC, the polymerization product may have a structure which is similar to that of a cell membrane. Therefore, the material comprising the predetermined polymer substrate, wherein an intended section of the surface of the substrate is coated with such a polymerization product formed by the graft polymerization, is useful as a biomaterial that is used for producing prosthesis or implanting in a living body. These materials are useful in the medical appliance which circulates and/or supplies blood or body fluid by being directly connected with the biotissues, for example, an artificial kidney, an artificial lung, a pump for artificial heart, a catheter and a cardiac pacemaker, in that the excellent biocompatibility thereof may be utilized then they are used as the material to form the parts that directly contacts with the biotissues including blood and body fluid.

A schematic diagram of the reaction in which PEEK is used as the substrate and MPC is used as the compound which has the phosphoryl choline group is shown below.

[Chemical formula 2]

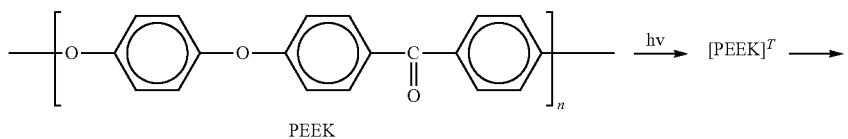

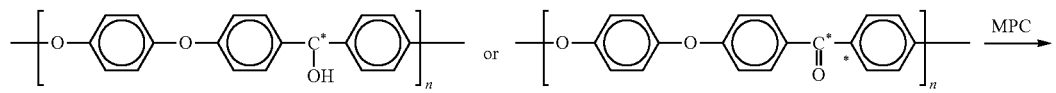

-continued

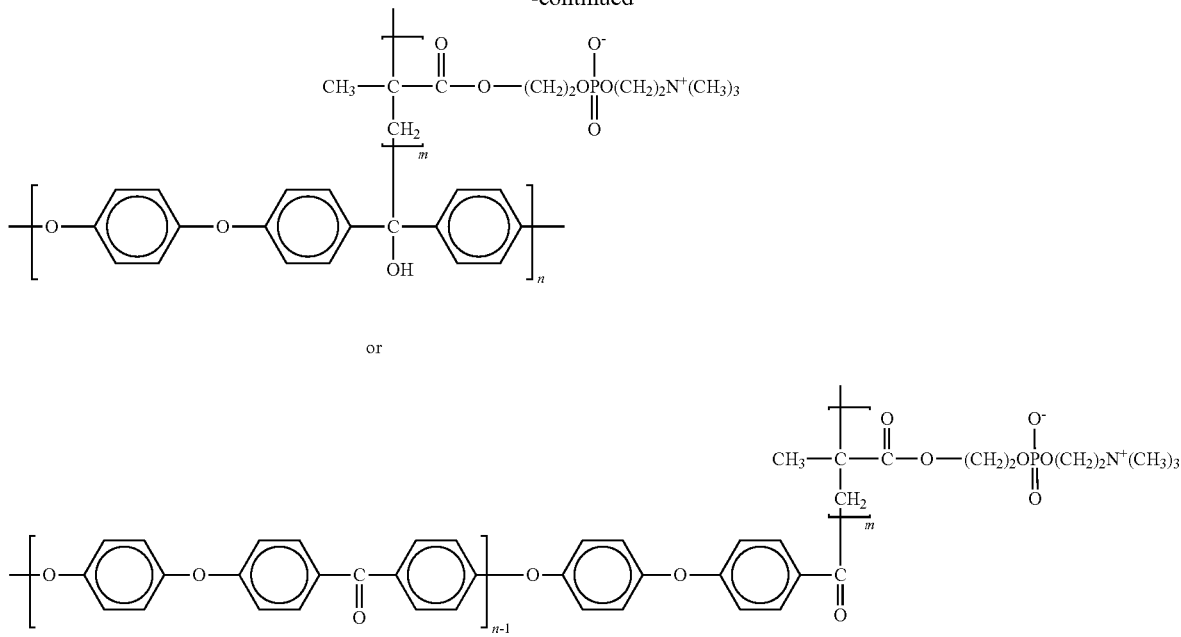

or

The solvents suitable for the present graft polymerization method include water, alcohols and aqueous solution of those alcohols. The solvent to be used is required to satisfy the conditions that at least the monomers are dissolved or dispersed therein; the substrate is neither eroded nor dissolved thereby; and the present graft polymerization will not be adversely affected thereby.

The light that can be used in the present graft polymerization method is an ultraviolet or a visible ray (hereinafter, also merely referred to as "UV ray"), which preferably has a wavelength in a range from 200 to 450 nm and more preferably has a wavelength in the range from 200 to 450 nm. The intensity of UV ray is preferably in a range from 1.5 to 8.0 mW/cm$^2$, for example, in a range from 4.0 to 6.0 mW/cm$^2$. It is preferable that the irradiation time is preferably in a range from 20 to 180 minutes and more preferably in a range from 45 to 90 minutes. The present photo-graft polymerization can be suitably performed according to the above conditions.

In the present graft polymerization method, radicals are generated by irradiating the intended surface of the polymer substrate with light energy during the graft polymerization reaction. Compared with the case using a radiation, it is easy to control the range of irradiation in the case using light. Therefore, it is possible to select the area where the graft polymerization is performed is limited to an intended section on the surface of the polymer substrate by using a mask and the like.

The polymerization product formed in the shape of a film on the surface of a polymer substrate can have the thickness in the range of 10 nm to 1 micrometer, for example, a thickness of 50 nm to 200 nm, depending of the necessity. The polymerization product formed on the surface of the polymer substrate through the present graft polymerization method generally has a thickness from 10 nm to 1 micrometer.

Accordingly, the ratio of the amount of the monomer to be used to the polymer substrate can be obtained by calculating the amount of the number of moles or the weight of the monomers that corresponds to the thickness of the coating of the polymerization product intended to be formed to the surface area of the polymer substrate to which the polymerization product intended to be attached. For example, it is capable of using an amount of from about 0.0001 to about 1.0 mol of the monomers per square cm of surface area of the polymer substrate.

Furthermore, the graft density (chains/nm$^2$) can be adjusted according to the conditions that are used in the polymerization. In the present invention, the graft density is preferably in the range from 0.01 to 0.6 chains/nm$^2$, particularly in the range from 0.05 to 0.6 chains/nm$^2$.

EXAMPLES

Example 1

Hereinafter, the method of performing the graft polymerization of the present invention will be illustrated in detail. In Example 1, PEEK was used as the substrate, MPC was used as the monomer and water was used as the solvent for suspending the monomers.

First, the PEEK specimen (length 10 cm×width 1 cm×thickness 0.3 cm; weight 3.9 g: trade name 450G (manufactured by VICTREX) used as the substrate was ultrasonically cleaned in ethanol, thereby the surface was cleaned. Separately, 0.5 mol/L aqueous solution of MPC was prepared. The above-prepared aqueous MPC solution was introduced into a quartz glass vessel in an amount of 15 mL.

While maintaining the temperature of the above aqueous MPC solution at 60° C., the PEEK specimen was immersed therein. The PEEK specimen was irradiated with UV ray having a wavelength of 300 to 400 nm for 90 minutes, thereby performed the graft polymerization reaction. After irradiating with ultraviolet rays, the PEEK specimen was picked up from the aqueous MPC solution, sufficiently rinsed with pure water and dried.

Example 2

In Example 2, the same procedure as Example 1 was performed except that a carbon fiber compound PEEK (CF- PEEK) sample (length 10 cm×width 1 cm×thickness 0.3 cm; weight 4.2 g: trade name CK4600 (manufactured by Sumitomo Chemical Co., Ltd.) as the substrate.

Comparative Example 1

In order to compare with Example 1, Comparative Example 1 was performed. In Comparative Example 1, the same procedure as Example 1 was performed except that a polyethylene (PE) sample (length 10 cm×width 1 cm×thickness 0.3 cm; weight 2.6 g: trade name GUR1020 (manufactured by POLY HI SOLIDUR) as the substrate.

Example 3

In Example 3, BP was added to the reaction system of Example 1 as the polymerization initiator. First, BP was dissolved in an acetone solution so that the concentration thereof becomes 10 g/L. After immersing in the obtained BP/acetone solution for 30 seconds, the PEEK specimen using as the substrate was picked up therefrom and dried, thereby a PEEK substrate on which surface BP was coated was obtained. Using this substrate, the graft polymerization reaction was performed in the same manner as the method of Example 1. The difference from Example 1 was the procedure that BP was applied onto the surface of substrate before the graft polymerization reaction.

Example 4

In Example 4, BP was added to the reaction system of Example 2 as the polymerization initiator. First, BP was dissolved in an acetone solution so that the concentration thereof becomes 10 g/L. After immersing in the obtained BP/acetone solution for 30 seconds, the CF-PEEK specimen using as the substrate was picked up therefrom and dried, thereby a CF-PEEK substrate on which surface BP was coated was obtained. Using this substrate, the graft polymerization reaction was performed in the same manner as the method of Example 1.

Comparative Example 2

In the comparative example 2, BP was used for the reaction system of the comparative example 1 as a polymerization initiator. It dissolved in the acetone solution so that it might become 10 g/L about BP at the beginning. After PE sample used for obtained BP/acetone solution as substrate was immersed for 30 seconds, PE substrate with which BP was applied to the surface was obtained by pulling up and drying an acetone solution. The graft polymerization reaction was made to perform like the method of Example 1 using this.

Each of the products from Example 1 and Example 3 was subjected to Fourier-transform infrared (FT-IR) analysis with total reflection method (ZnSe prism) by using FT-IR analyzer Type 615 (manufactured by JASCO Co. Ltd.) at a resolution of 4 cm$^{-1}$ for 32 times of integration. The results are shown in FIG. 1.

Figure 1A:
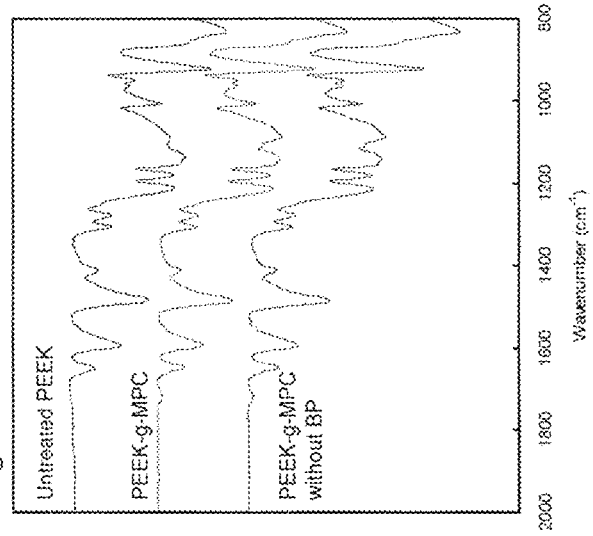

FIG. 1a shows, from the top thereof sequentially, the results of PEEK used as the substrate (thus untreated), MPC graft polymerized PEEK product (PEEK-g-MPC, where BP was used) obtained from Example 3, and MPC graft polymerized PEEK product (PEEK-g-MPC, where BP was not used) obtained from Example 1 without using BP, respectively. From FIG. 1a, it has been confirmed that each PEEK substrate in each product obtained from Example 1 and Example 3 has not been deteriorated through each operation. FIG. 1b indicates the difference of the spectrum chart of the PEEK used as the substrate (thus untreated) from the spectrum chart of the MPC graft polymerized PEEK product (PEEK-g-MPC, where BP was not used) obtained from Example 1 without using BP by overlapping them. From FIG. 1b, the peaks (1060 or 1720 cm$^{-1}$) derived from MPC were found on the surface of the PEEK product obtained from Example 1 where the graft polymerization was performed without using the photopolymerization initiator (BP). Therefore, it could be confirmed that MPC could be graft polymerized on the surface of the PEEK in the case where the photopolymerization initiator was not used.

The product from Example 1 was subjected to XPS analysis using an XPS spectrophotometer (AXIS-HSi165; manufactured by KRATOS ANALYTICAL) equipped with a 15-kV Mg K-alpha radiation source under the conditions using applied voltage of 15 kV and photoelectron emission angle of 90 degrees. The results of the obtained spectral analysis is shown in FIG. 2. In addition, the results of the surface elemental composition is shown in Table 1.

From FIG. 2a, the peak (C=O) derived from MPC was found in any of the PEEK surface (Example 3 (PEEK-g-MPC)) that was subjected to the graft polymerization using the photopolymerization initiator (BP) and the PEEK surface (Example 1 (PEEK-g-MPC, where BP was not used) that was subjected to the graft polymerization without using the photopolymerization initiator. Therefore, it could be confirmed that MPC also could be graft polymerized on the surface of the PEEK in the case where the photopolymerization initiator was not used.

From FIG. 2c, the peak (—N$^+$(CH$_3$)$_3$) derived from MPC was found in any of the PEEK surface that was subjected to the graft polymerization using the photopolymerization initiator (BP) and the PEEK surface that was subjected to the graft polymerization without using the photopolymerization initiator. Therefore, it could be confirmed that MPC also could be graft polymerized on the surface of the PEEK in the case where the photopolymerization initiator was not used. From FIG. 2d, the peak (P—O) derived from MPC was found in any of the PEEK surface that was subjected to the graft polymerization using the photopolymerization initiator (BP) and the PEEK surface that was subjected to the graft polymerization without using the photopolymerization initiator. Therefore, it could be confirmed that MPC also could be graft polymerized on the surface of the PEEK in the case where the photopolymerization initiator was not used. In each of N$_1$, spectrum and P$_{2p}$ spectrum, the peak derived from MPC was found in the graft polymerized PEEK surface irrespective of the presence or absence of the photopolymerization initiator.

TABLE 1

XPS Analysis (Atomic Concentration) (n = 5)

| | Sample | Surface elemental composition (atom %) | | | |
|---|---|---|---|---|---|
| | | $C_{1s}$ | $O_{1s}$ | $N_{1s}$ | $P_{2p}$ |
| | PE (untreated) | 99.8 (0.3)** | 0.2 (0.3) | 0.0 (0.0) | 0.0 (0.0) |
| Comparative Example 2 | PE-g-MPC | 58.0 (0.2) | 31.5 (0.2) | 5.2 (0.1) | 5.3 (0.1) |
| Comparative Example 1 | PE-g-MPC (without BP) | 97.3 (0.5) | 2.6 (0.5) | 0.0 (0.0) | 0.1 (0.1) |
| | PEEK (untreated) | 83.2 (0.5) | 16.7 (0.5) | 0.1 (0.1) | 0.0 (0.0) |
| Example 3 | PEEK-g-MPC | 64.5 (1.1) | 25.2 (0.8) | 5.1 (0.2) | 5.2 (0.2) |

TABLE 1-continued

XPS Analysis (Atomic Concentration) (n = 5)

| | Sample | Surface elemental composition (atom %) | | | |
|---|---|---|---|---|---|
| | | $C_{1s}$ | $O_{1s}$ | $N_{1s}$ | $P_{2p}$ |
| Example 1 | PEEK-g-MPC | 62.5 | 27.3 | 5.1 | 5.1 |
| | (without BP) | (0.6) | (0.5) | (0.1) | (0.1) |
| | CF-PEEK | 81.7 | 16.4 | 1.6 | 0.3 |
| | (untreated) | (0.6) | (0.5) | (0.2) | (0.1) |
| Example 4 | CF-PEEK-g-MPC | 62.9 | 27.4 | 5.3 | 4.4 |
| | | (1.3) | (1.0) | (0.2) | (0.2) |
| Example 2 | CF-PEEK-g-MPC | 63.5 | 26.9 | 5.3 | 4.4 |
| | (without BP) | (1.0) | (0.8) | (0.2) | (0.3) |
| | MPCpolymer* | 57.9 | 31.6 | 5.3 | 5.3 |

*Theoretical elemental composition of MPCpolymer
**The standard deviation is in parentheses.

It was confirmed from Table 1 that, with regard to the atomic concentration on the surface of the product obtained through the graft polymerization of MPC onto PEEK, the atomic concentration on the surface of the product obtained from Example 1 wherein no photopolymerization initiator was used is found to be substantially equivalent to that of the product obtained from Example 3 wherein photopolymerization initiator was used. In addition, nitrogen and phosphorus are the elements derived from MPC and it is shown that each atomic concentration of nitrogen and phosphorus is substantially equivalent to that of the theoretical value of MPC copolymer in each product of Example 1 and Example 3. On the other hand, with regard to the atomic concentration on the surface of the product obtained through the graft polymerization of MPC onto PEEK, a significant difference was found between the product obtained from Comparative Example 1 wherein no photopolymerization initiator was used and the product obtained from Comparative Example 2 wherein photopolymerization initiator was used. It was confirmed that the surface atomic concentration of the product from the Comparative Example 1 was substantially equivalent to the surface atomic concentration of untreated PE. In addition, with regard to the atomic concentration on the surface of the product obtained through the graft polymerization of MPC onto CF-PEEK, the atomic concentration on the surface of the product obtained from Example 2 wherein no photopolymerization initiator was used is found to be substantially equivalent to that of the product obtained from Example 4 wherein photopolymerization initiator was used.

Figure 3:
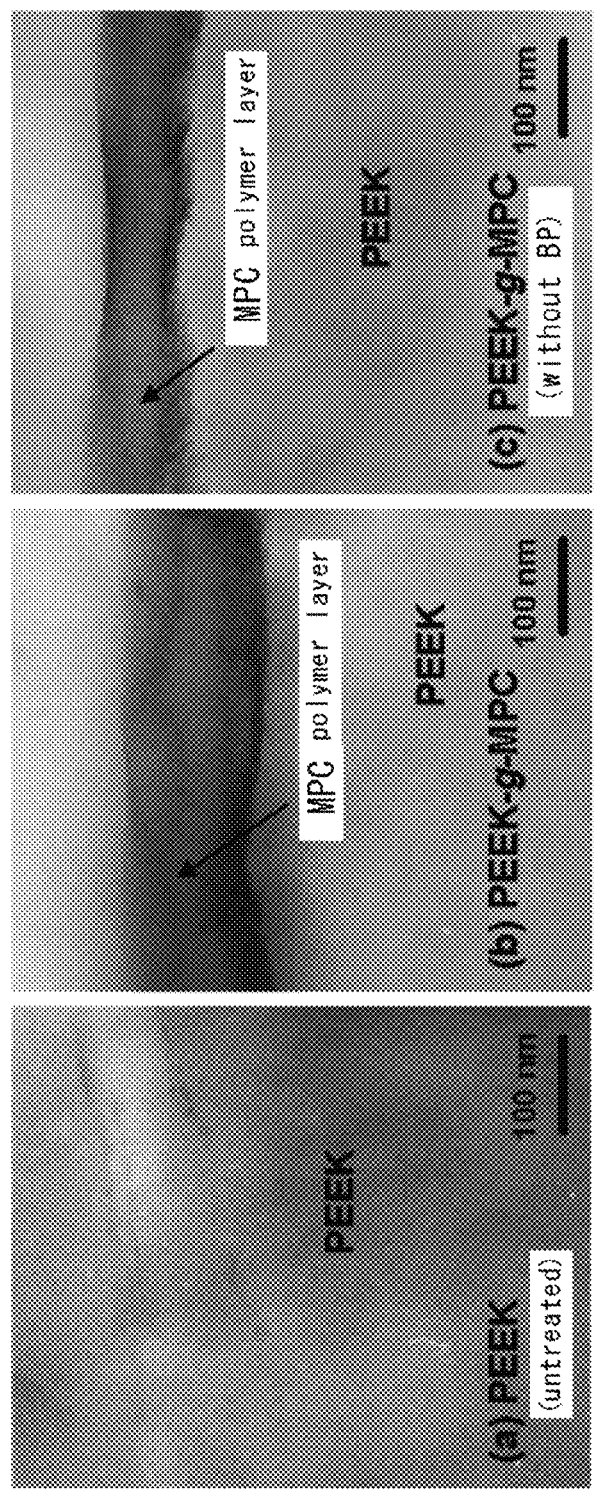
FIG. 3 shows the result of TEM images of each cross section of the products of Example 1 and Example 3.

On the surface of the product of Example 1 and Example 3, the thickness of the MPC polymer membrane obtained through the graft polymerization was measured. The specimen to be used for the measurement was embedded in an epoxy resin, subjected to ruthenium tetrachloride dyeing, and then ultrathin sections were sliced therefrom using an ultramicrotome. Using transmission electron microscope (TEM), Model JEM-1010 (manufactured by JEOL), observation was conducted at an acceleration voltage of 200 kV. The results are shown in FIG. 3. In FIG. 3, untreated PEEK is (a), Example 3 is (b) and Example 1 is (c).

In FIG. 3, a coating layer (MPC polymer film) or biocompatible material layer was observed on the surface of Example 1 and Example 3, which was not observed in the untreated PEEK. Each thickness of the layer (MPC polymer film) of the product from Examples 1 and 3 was about 100 nm.

Each static water-contact angle of the products of Examples 1-4 and Comparative Examples 1-2 was measured with an optical bench-type contact angle goniometer (model DM300; Kyowa Interface Science Co., Ltd., Japan) using a sessile drop method according to ISO Standard 15989 under the conditions in which drops of purified water (1 µL) were deposited on each surface of the products and the contact angle was measured after 60 seconds. As a basis for comparison, the static water-contact angle was similarly measured in the untreated state with regard to each polymer substrate. The results are shown in FIG. 4.

Figure 4:
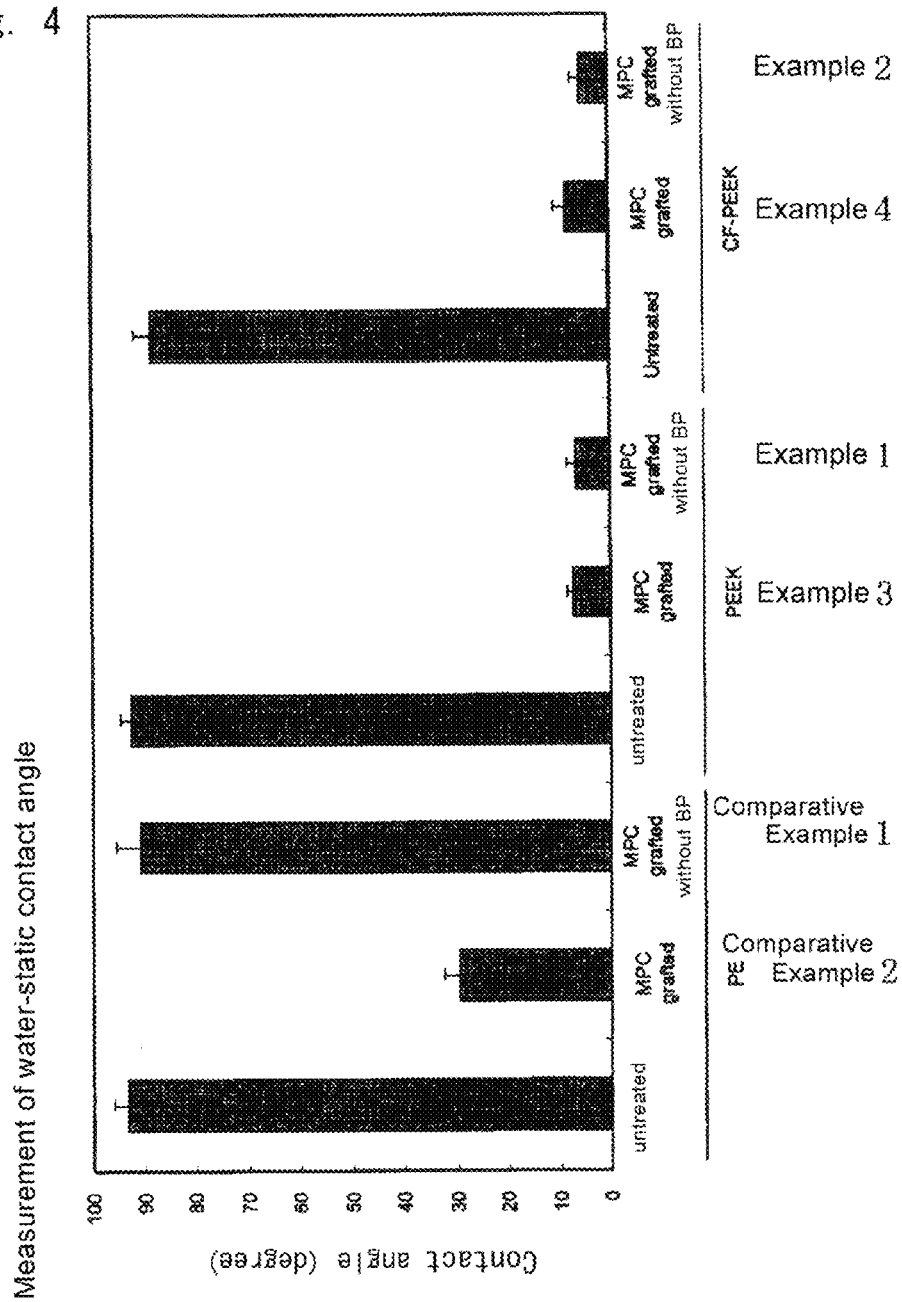
FIG. 4 shows the results of measurements of water-static contact angle on the untreated substrate and the treated substrates with/without using the polymerization initiator, using PE substrate, PEEK substrate and CF-PEEK substrate.

It was confirmed from FIG. 4 that the water-contact angle on the surface of the product significantly decreased irrespective of the presence or absence of the photopolymerization initiator with regard to each product from Example 1 and Example 3, each of which was obtained through the graft polymerization of MPC onto PEEK substrate. Similarly, it was confirmed that the water-contact angle on the surface of the product significantly decreased irrespective of the presence or absence of the photopolymerization initiator with regard to each product from Example 2 and Example 4, each of which was obtained through the graft polymerization of MPC onto CF-PEEK substrate.

According to the results from Comparative Examples 1 and 2, wherein PE was used as the substrate, the contact angle value of the product from Comparative Example 1, which was obtained by performing the graft polymerization of the MPC to PE substrate without using the photopolymerization initiator was larger than that of the product from Comparative Example 2, which was obtained by performing the graft polymerization of the MPC to PE substrate with using the photopolymerization initiator, and was rather similar to the contact angle value of the untreated PE substrate. From this, it has been shown that the substrate which has no ketone group on the surface thereof is, particularly, not suitable for the method of the present invention wherein a monomer is graft polymerized to a substrate without using a photopolymerization initiator.

Each dynamic friction coefficient of the products of Examples 1-4 and Comparative Examples 1-2 was measured with using a Pin-on-plate type friction tester (Tribostation Type 32, produced by Shinto Science Co., Ltd.) at the load of 0.98N, the sliding velocity of 50 mm/second, the slide distance of 25 mm, the bounce frequency of 1 Hz, the room temperature and the water lubrication environmental condition. As a basis for comparison, the dynamic friction coefficient was similarly measured in each of the polymer substrate in each untreated state. The results are shown in FIG. 5.

Figure 5:
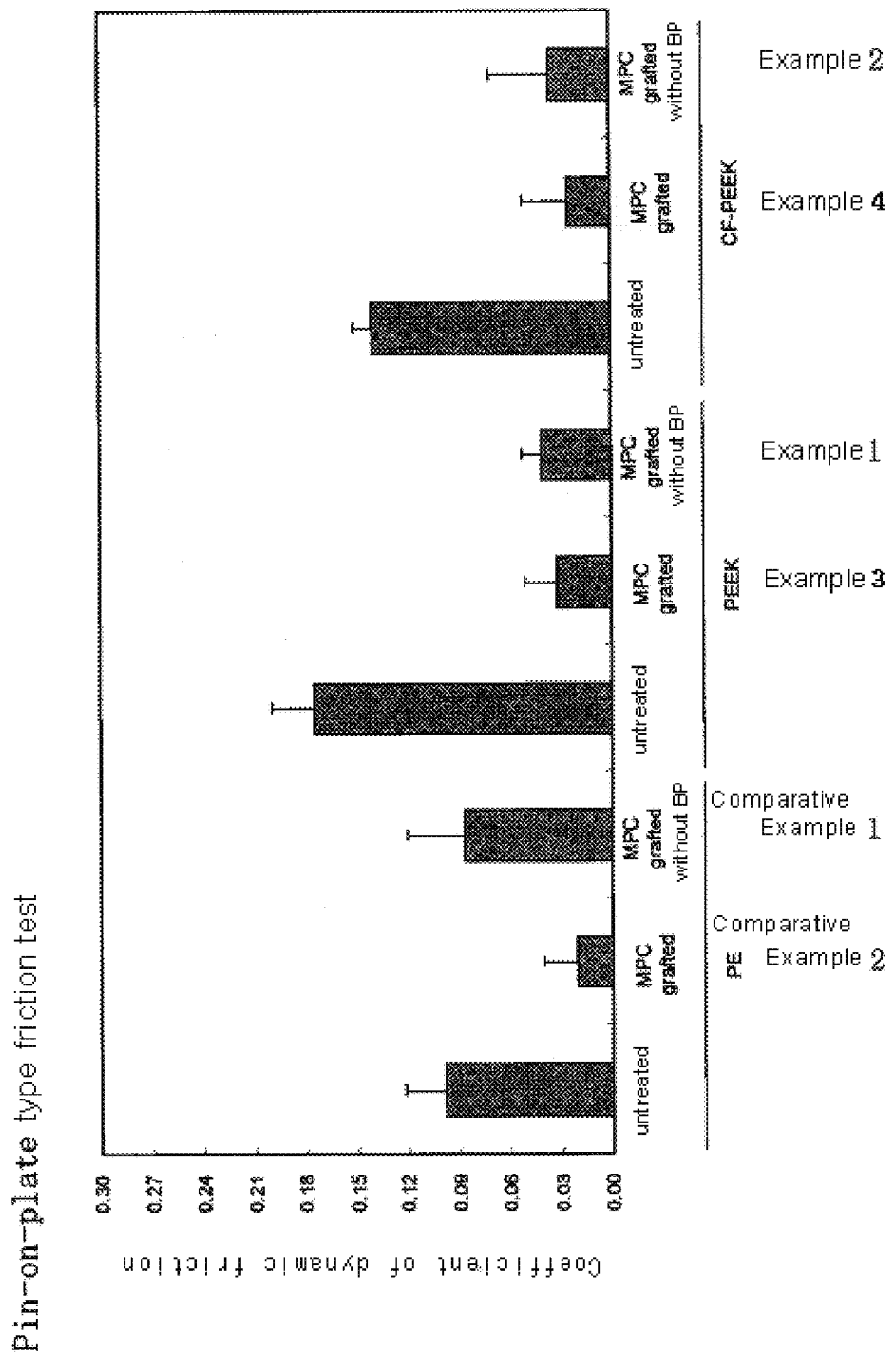
FIG. 5 shows the results of measurements of coefficient of dynamic friction using Pin-on-plate type friction tester on the untreated substrate and the treated substrates with/without using the polymerization initiator, using PE substrate, PEEK substrate and CF-PEEK substrate.

It was confirmed from FIG. 5 that the dynamic friction coefficient on the surface of the coating layer (or biocompatible material layer) significantly decreased irrespective of the presence or absence of the photopolymerization initiator in Examples where PEEK substrate is used as the substrate. In an example where PE is used as the substrate, the decrease of the dynamic friction coefficient was observed merely in the case where the photopolymerization initiator was used (Example 2), and no decrease of the dynamic friction coefficient was observed in the case where the photopolymerization initiator was not used (Comparative Example 1). Therefore, it could be confirmed that a sliding member having an coating layer with a low coefficient of dynamic friction (or biocompatible material layer) may be produced by graft polymerization of MPC to PEEK substrate.

Figure 6:
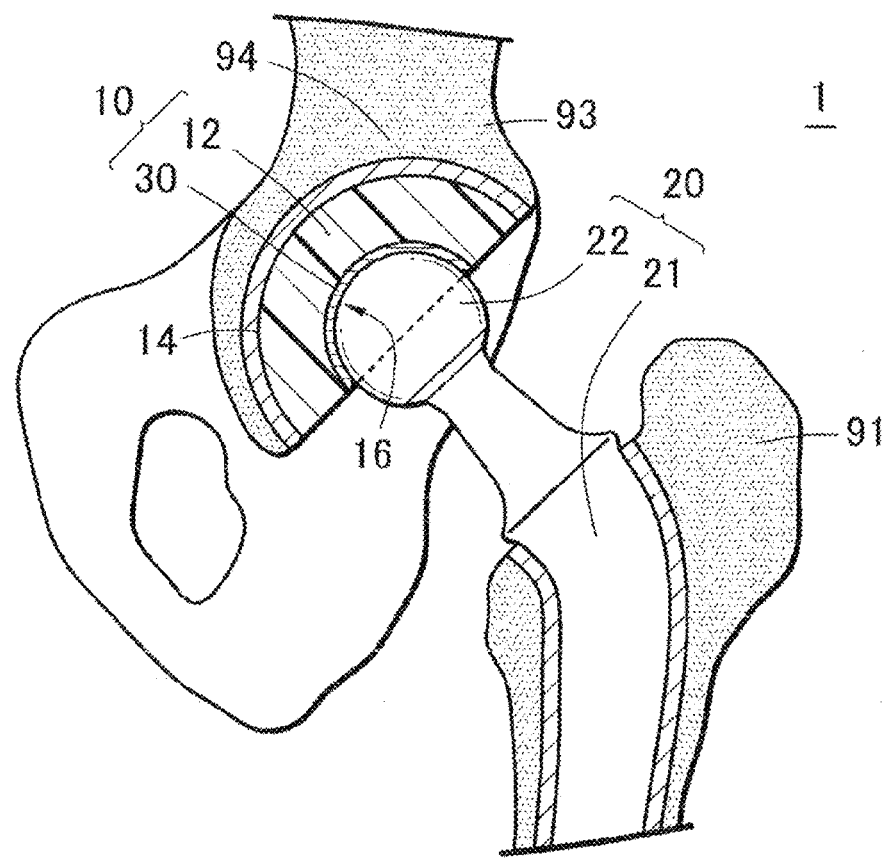
FIG. 6 is a schematic illustration of an example where the construction of Example 1 is applied to an artificial hip joint.

FIG. 6 is a schematic illustration of an artificial hip joint 1, which is one of the artificial joints produced using the artificial joint component of the present invention. The artificial hip joint 1 comprises a sliding member (an acetabular cup) fixed within an acetabular 94 in a coxal bone 93, and a femoral stem 20 fixed to the proximal end of a femur 91. The acetabular cup 10 comprises a cup substrate 12 which has an acetabular fixing face 14 having almost hemispherical shape and a sliding face 16 having almost hemispherical hollow shape, and a coated layer 30 which coats the sliding face 16. The artificial joint 1 functions as an artificial hip joint by inserting a ball head 22 of the femoral stem 20 into the sliding face 16 of the acetabular cup 10, thereby the both components being able to slidably move with each other.

According to Example 1, using PEEK as the cup substrate 12 and MPC as the monomer, a coating layer 30 was graft polymerized onto the surface to become the sliding face 16 of the cup substrate 12. In this artificial hip joint, favorable slidability and movability (anti-dislocation function) could be attained even when the thickness of the coating layer 30 was preferably made to be 50 to 200 nm, the thickness of the cup substrate 12 was preferably made to be 3 to 6 mm, and the diameter of the ball head 22 was preferably made to be 40 to 48 mm.

Figure 7C:
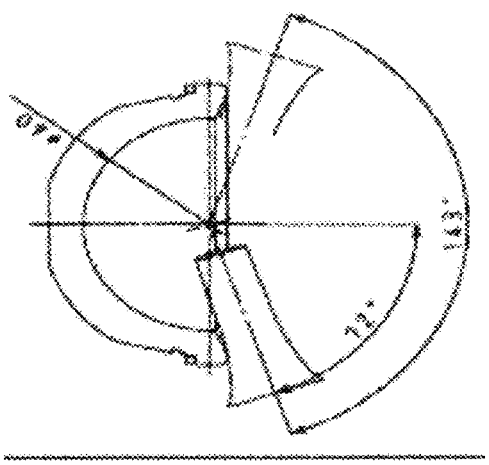
FIG. 7 is schematic illustrations showing each motion range of examples where the construction of Example 1 is applied to an artificial hip joint.
Figure 7B:
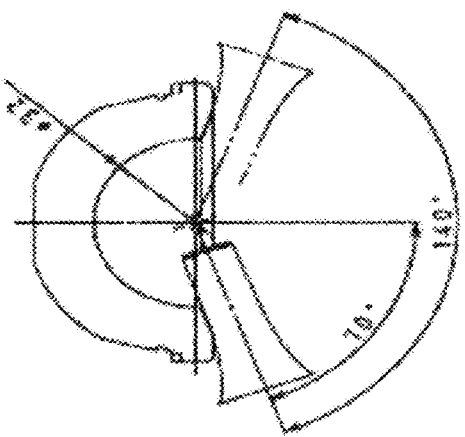
Figure 7A:
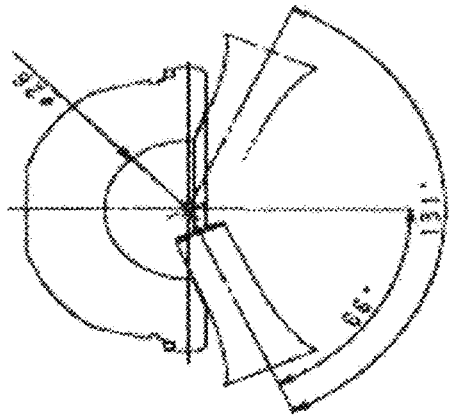

FIG. 7 shows a schematic illustration of the range of motion of the artificial joint component of the present invention. FIG. 7 (*a*) shows an example where a diameter of 26 mm was adopted as the ball head which is the maximum size for corresponding to the thickness 13 mm of the cup substrate. FIG. 7(*b*) shows an example where a diameter of 32 mm was adopted as the ball head which is the maximum size for corresponding to the thickness 10 mm of the cup substrate. FIG. 7(*c*) shows an example where a diameter of 40 mm was adopted as the ball head which is the maximum size for corresponding to the thickness 6 mm of the cup substrate.

It was confirmed that, in the order of FIG. 7(*a*), FIG. 7 (*b*) and FIG. 7(*c*), the thickness of the cup substrate decreased and the diameter of the ball head increased, and the range of motion of the artificial joint component increased. Specifically, in the example of FIG. 7 (*a*) which corresponds to the conventional artificial joint having 26 mm sized diameter of the ball head and 13 mm sized thickness of the cup substrate, the range of motion was 131°. In the case of FIG. 7(*a*), which is an example of the present invention, the diameter of the ball head was 32 mm and the thickness of the cup substrate was 10 mm, and the range of motion was 140°. In the case of FIG. 7(*c*), which is another example of the present invention, the diameter of the ball head was 40 mm and the thickness of the cup substrate was 6 mm, and the range of motion was 143°. The matter that the range of motion of an artificial joint increases means that the artificial joint has a structure which hardly dislocates. The thickness of the cup substrate was conventionally required to be 10 mm or more according to the limitation from the strength thereof, since PE was used as the substrate thereof. However, using a polymer having higher strength such as PEEK as the present invention, a cup having a thickness of 3 to 6 mm may be designed and a sufficient safety relating to the strength can also be secured.

From the above explanation, it was confirmed that the monomers having phosphoryl choline groups and vinyl groups such as acrylates may be graft polymerized onto the surface of the polymer substrate having ketone groups thereon by irradiating with light, and the surface of the artificial joint component produced thereby has a low water-contact angle and a low coefficient of dynamic friction. In addition, it was also confirmed that the artificial joint produced using those artificial joint components could have a structure having a wide range of motion. Therefore, an artificial joint simultaneously having a high lubricity, a biocompatibility and an anti-dislocation function can be provided by applying the polymer sliding component of the present invention.

Each protein (albumin) adsorption test of the products of Examples 1 and 3 and Comparative Examples 1 and 2 was measured according to a colorimetric determination method (micro BCA method) using coordination of reduced Cu(+) from Biuret reaction and bicinchoninic acid (BCA) with using high-sensitivity BCA protein assay reagent (BCA-200 Protein Assay Kit) (produced by Thermo Fisher Scientific Inc.) at a condition of 37° C. for 1 hour of adsorption time. As a basis for comparison, the same test was performed in each of the polymer substrate in each untreated state. The results are shown in FIG. 8.

Figure 8:
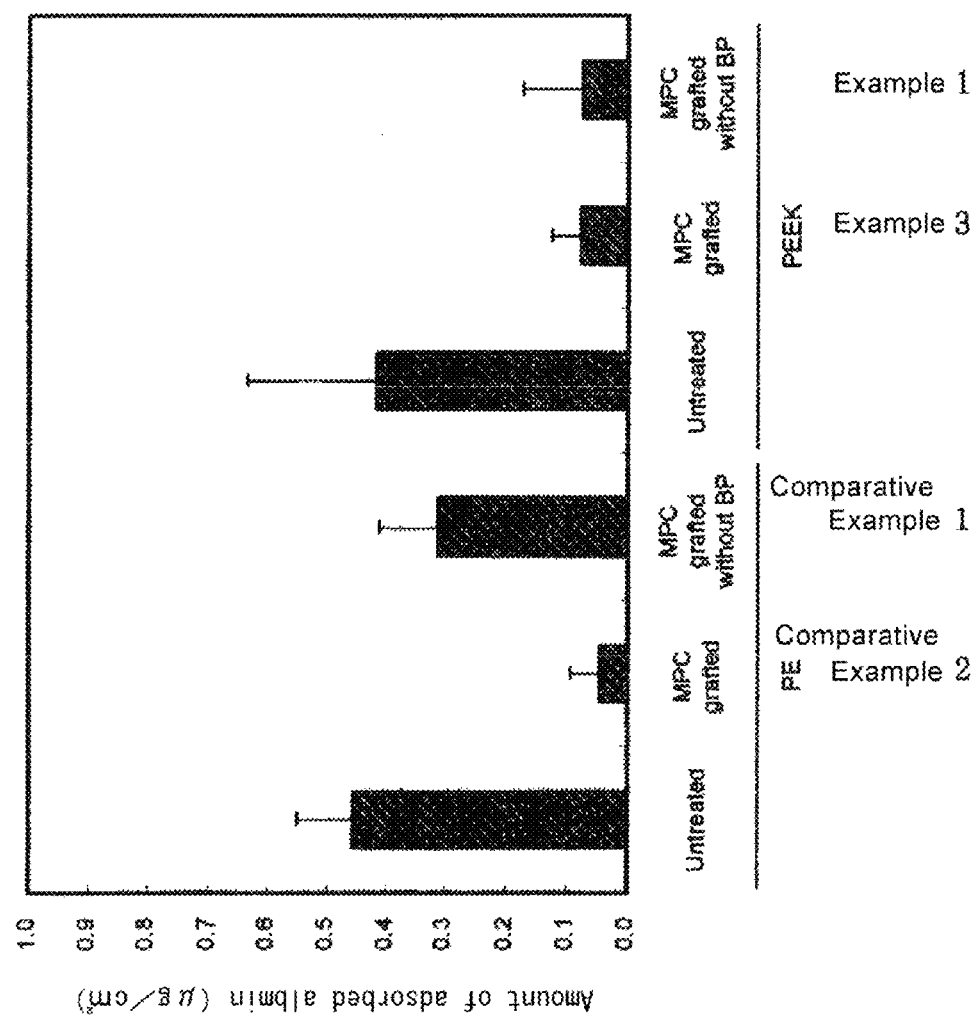
FIG. 8 shows the results of measurements of protein (albumin) adsorption test performed on the untreated substrate and the treated substrates with/without using the polymerization initiator, using PE substrate, PEEK substrate and CF-PEEK substrate.

From FIG. 8, it was confirmed that the adsorption of protein (albumin) of the surface of the biocompatible material layer significantly decreased irrespective of the presence or absence of the photopolymerization initiator in Examples where PEEK substrate is used as the substrate (Examples 1 and 3) compared with an untreated PEEK substrate. In addition, in the Examples where PE were used as the substrates, the decrease of the adsorption of protein (albumin) was found merely in the case where the polymerization initiator was used (comparative example 2), but the decrease of the adsorption of protein (albumin) was not found in the case where the polymerization initiator was not used (comparative example 1). Therefore, it was confirmed that a medical appliance material which has a biocompatible material layer having a low adsorption of protein (albumin) can be produced by graft polymerizing MPC to PEEK substrate.

Each protein (fibrinogen) adsorption test of the products of Examples 1 and 3 was measured according to the micro BCA method with using high-sensitivity BCA protein assay reagent (BCA-200 Protein Assay Kit) (produced by Thermo Fisher Scientific Inc.) at a condition of 37° C. for 1 hour of adsorption time. As a basis for comparison, the same test was performed in each of the polymer substrate in each untreated state. The results are shown in FIG. 9.

Figure 9:
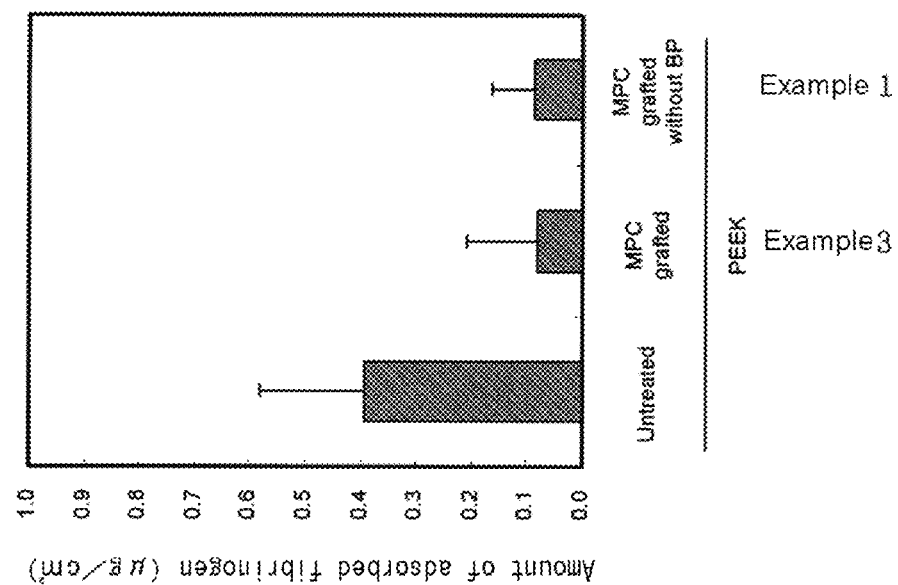
FIG. 9 shows the results of measurements of protein (fibrinogen) adsorption test performed on the untreated substrate and the treated substrates with/without using the polymerization initiator, using PEEK substrate.

From FIG. 9, it was confirmed that the adsorption of protein (fibrinogen) of the surface of the biocompatible material layer significantly decreased irrespective of the presence or absence of the photopolymerization initiator in Examples 1 and 3 compared with an untreated PEEK substrate. Therefore, it was confirmed that a medical appliance material which has a biocompatible material layer having a low adsorption of protein (fibrinogen) can be produced by graft polymerizing MPC to PEEK substrate.

From the above explanation, it was confirmed that the monomers having phosphoryl choline groups and vinyl groups such as acrylates may be graft polymerized onto the surface of the polymer substrate having ketone groups thereon by irradiating with light, and the surface of the medical appliance material produced thereby has significantly low adsorption of protein (albumin or fibrinogen). Therefore, it was confirmed that the medical appliance and the medical appliance material of the present invention can demonstrate excellent properties in an anti-thrombus property, a cellular adhesion inhibiting potency, a biocompatibility, antibacterial properties (inhibition of biofilm formation and adhesion) and so on.

INDUSTRIAL APPLICABILITY

The polymer sliding material of the present invention is suitable to apply to an artificial joint component. The artificial joint component of the present invention is suitable to apply to an artificial joint. The acetabular cup which was produced using the artificial joint component of the present invention makes the ball head having a size, which was not conventionally considered to be adequate, available to be used, since it makes the thickness of the acetabular cup per se thin. Therefore, an artificial joint having enlarged range of motion and begin useful for prevention of dislocation may be provided, which is valuable for the medical industry.

The medical appliance material (biocompatible polymeric material) of the present invention is suitably applicable to a medical appliance, and in detail, an appliance which contacts with blood and the biotissues inside and/or outside of the body, for example, an artificial kidney, an artificial lung, an artificial trachea, a blood pump for an (auxiliary) artificial heart, an artificial valve, an artificial blood vessel, a catheter, a cardiac pacemaker, an artificial bone, an artificial tendon, an artificial knuckle and a bone securing plate, a bone screw and so on, and a dentistry implant. It is capable of providing a medical appliance excellent in the antithrombotic property and the slidability, which hardly forms thrombus and the like, thereby for example, being capable of eliminating use of the drugs inhibiting a biological defense reaction, even where the appliance is used within the living body for a long period of time, and thus being valuable for the medical industry. In particular, in the dentistry field, it is capable of providing a medical appliance as a dental implant, which demonstrates cellular adhesion inhibiting effect and which is capable of inhibiting the periodontal diseases and the deposition of dental plaque, and thus being valuable for the medical industry.

The invention claimed is:

1. A polymer sliding material comprising a polymer substrate (A) having ketone groups on the surface thereof and a coating layer (B) which coats at least a portion of the surface of the polymer substrate (A), wherein the coating layer (B) is formed by a surface graft polymerization comprising immersing the polymer substrate (A) in a reaction system containing a monomer (C), irradiating the polymer substrate (A) with light which is an ultraviolet ray or a visible ray, thereby polymerizing the monomer from the surface of the substrate.

2. The polymer sliding material according to claim 1, wherein the coating layer (B) is formed through the graft polymerization without including a polymerization initiator in the surface and inside of the polymer substrate (A) and the reaction system containing the monomer (C).

3. The polymer sliding material according to claim 1, wherein the polymer substrate (A) is the polymer substrate having an aromatic ketone.

4. The polymer sliding material according to claim 1, wherein the polymer substrate (A) is a polymer selected from the group consisting of polyether ketone (PEK), polyetherether ketone (PEEK), polyether ketone ketone (PEKK), Polyetheretherketone ketone (PEEKK), polyether ketone ether ketone ketone (PEKEKK) and poly aryl ether ketone (PAEK), a composited polymer wherein at least two kinds of polymers from the above group are composited, and a fiber-reinforced polymer formed by a polymer selected from the above polymer and the composited polymer.

5. The polymer sliding material according to claim 1, wherein the monomer (C) is selected from (meth)acrylate compounds.

6. The polymer sliding material according to claim 1, wherein the monomer (C) contains a compound having a phosphoryl choline group.

7. The polymer sliding material according to claim 6, wherein the compound having the phosphoryl choline group is 2-methacryloyloxyethyl phosphorylcholine (MPC).

8. The polymer sliding material according to claim 1, wherein the coating layer (B) has a thickness of 10 to 200 nm.

9. The polymer sliding material according to claim 1, wherein the surface of the sliding material shows a static water-contact angle of not more than 20° using a sessile drop method under the conditions in which the contact angle was measured after 60 seconds.

10. The polymer sliding material according to claim 1, wherein each concentration of a phosphorus atom and a nitrogen atom on the surface of the sliding material measured by X-ray photoelectron spectroscopy is not less than 4 atom %.

11. An artificial joint component made of a polymer sliding material according to claim 1, wherein a polymer substrate (A) constructs the proximal of the artificial joint component, and a coating layer (B) is formed on at least the sliding face of the artificial joint component.

12. The artificial joint component according to claim 11, wherein the ball head to be combined has a thickness of not less than 32 mm and the polymer substrate has a thickness in the range from 3 to 6 mm.

13. An artificial joint, which is made of the artificial joint component of claim 11.

14. A medical appliance material comprising a biocompatible material layer (B) covering at least a portion of the surface of the polymer substrate (A) having ketone groups on the surface thereof, wherein the biocompatible material layer (B) is formed by a surface graft polymerization comprising immersing the polymer substrate (A) in a reaction system containing a monomer (C), irradiating the polymer substrate (A) with light which is an ultraviolet ray or a visible ray, thereby polymerizing the monomer from the surface of the substrate.

15. The medical appliance material according to claim 14, wherein the coating layer (B) is formed through the graft polymerization without including a polymerization initiator in the surface and inside of the polymer substrate (A) and the reaction system containing the monomer (C).

16. The medical appliance material according to claim 14, wherein the polymer substrate (A) is the polymer substrate having an aromatic ketone.

17. The medical appliance material according to claim 14, wherein the polymer substrate (A) is a polymer selected from the group consisting of polyether ketone (PEK), polyetherether ketone (PEEK), polyether ketone ketone (PEKK), Polyetheretherketone ketone (PEEKK), polyether ketone ether ketone ketone (PEKEKK) and poly aryl ether ketone (PAEK), a composited polymer wherein at least two kinds of polymers from the above group are composited, and a fiber-reinforced polymer formed by a polymer selected from the above polymer and the composited polymer.

18. The medical appliance material according to claim 14, wherein the monomer (C) is selected from (meth)acrylate compounds.

19. The medical appliance material according to claim 14, wherein the monomer (C) contains a compound having a phosphoryl choline group.

20. The medical appliance material according to claim 19, wherein the compound having the phosphoryl choline group is 2-methacryloyloxyethyl phosphorylcholine (MPC).

21. The medical appliance material according to claim 14, wherein the biocompatible material layer (B) has a thickness of 10 to 200 nm.

22. The medical appliance material according to claim 14, wherein the surface of the biocompatible material layer (B) shows a static water-contact angle of not more than 20° using a sessile drop method under the conditions in which the contact angle was measured after 60 seconds.

23. The medical appliance material according to claim 14, wherein each concentration of a phosphorus atom and a nitrogen atom on the surface of the biocompatible material layer (B) measured by X-ray photoelectron spectroscopy is not less than 4 atom %.

24. The medical appliance material according to claim 14, wherein the adsorption of protein (albumin or fibrinogen) of the surface of the biocompatible material layer (B) obtained through the micro BCA method is not more than 0.1 microgram/cm$^2$.

25. A medical appliance made of the medical appliance material according to claim 14.

26. The medical appliance according to claim 25 selected from the group consisting of an artificial kidney, an artificial lung, an artificial trachea, a blood pump for an (auxiliary) artificial heart, an artificial valve, an artificial blood vessel, a catheter, a cardiac pacemaker, dental implant, an artificial tooth, an artificial bone, an artificial tendon, an artificial knuckle and a bone securing plate, a bone screw and so on.

27. A method of producing a medical appliance material comprising a polymer substrate (A) and a coating layer (B) which coats at least a portion of the surface of the polymer substrate (A), the method comprising immersing a polymer substrate (A) in a reaction system containing a monomer (C) for forming a biocompatible material layer (B), irradiating the polymer substrate (A) with light which is an ultraviolet ray or a visible ray, thereby initiating the polymerization of the monomer from the surface of the polymer substrate (A), wherein the polymer substrate (A) is a polymer having ketone groups on the surface thereof, and the reaction system containing the monomer (C) as well as the surface and the inside of the polymer substrate (A) includes no polymerization initiator.

28. The polymer sliding material according to claim 1, wherein the light has a wavelength in a range from 200 nm to 450 nm.

29. The medical appliance material according to claim 14, wherein the light has a wavelength in a range from 200 nm to 450 nm.

30. The method according to claim 27, wherein the light has a wavelength in a range from 200 nm to 450 nm.

* * * * *